United States Patent
Ghumro et al.

(10) Patent No.: US 10,577,327 B2
(45) Date of Patent: Mar. 3, 2020

(54) PYRIDINE BASED IONIC FLUORIDE FOR CATALYZING INDOLE AND TETRAZOLE FORMATION

(71) Applicant: King Abdulaziz University, Jeddah (SA)

(72) Inventors: Sarfaraz Ali Ghumro, Jeddah (SA); Rima D. Alharthy, Jeddah (SA); Sana Saleem, Jeddah (SA); Mariya Al-Rashida, Jeddah (SA); Nafees Iqbal, Jeddah (SA); Shakil Ahmed, Jeddah (SA); Syed Abid Ali, Jeddah (SA); Syed Tarique Moin, Jeddah (SA); Abdul Hameed, Jeddah (SA)

(73) Assignee: King Abdulaziz University, Jeddah (SA)

( * ) Notice: Subject to any disclaimer, the term of this patent is extended or adjusted under 35 U.S.C. 154(b) by 0 days.

(21) Appl. No.: 16/004,511

(22) Filed: Jun. 11, 2018

(65) Prior Publication Data

US 2019/0375711 A1    Dec. 12, 2019

(51) Int. Cl.
| | |
|---|---|
| *C07D 213/74* | (2006.01) |
| *C07D 209/88* | (2006.01) |
| *B01J 31/02* | (2006.01) |
| *C07D 257/04* | (2006.01) |
| *C07D 209/86* | (2006.01) |

(52) U.S. Cl.
CPC ........ *C07D 213/74* (2013.01); *B01J 31/0284* (2013.01); *C07D 209/86* (2013.01); *C07D 209/88* (2013.01); *C07D 257/04* (2013.01)

(58) Field of Classification Search
None
See application file for complete search history.

(56) References Cited

U.S. PATENT DOCUMENTS 9,643,169 B1    5/2017    Hameed et al.

FOREIGN PATENT DOCUMENTS

| EP | 2 319 621 A2 | 5/2011 | |
| EP | 2660196 A1 * | 11/2013 | ........... C07C 303/40 |
| JP | 4961689 B2 | 6/2012 | |
| KR | 10-2016-0018546 | 2/2016 | |

OTHER PUBLICATIONS

Barlin et al, Journal of the Chemical Society Section (B) , Physical Organic, (8), pp. 1675-1682 (Year: 1971).*
Hameed et al, Tetrahedron, vol. 72, pp. 2763-2812 (Year: 2016).*
Devdutt Chaturvedi, "Ionic Liquids: A Class of Versatile Green Reaction Media for the Syntheses of Nitrogen Heterocycles" Current Organic Synthesis, vol. 8, No. 3, 2011, pp. 438-471.

* cited by examiner

*Primary Examiner* — Zinna Northington Davis
(74) *Attorney, Agent, or Firm* — Oblon, McClelland, Maier & Neustadt, L.L.P.

(57) ABSTRACT

A pyridine based ionic liquid with a fluoride counter anion which catalyzes Fischer indole reaction and click chemistry. Methods of preparing the ionic liquid, and methods of utilizing the ionic liquid as a catalyst to synthesize indoles/indolenines and tetrazoles are also provided.

13 Claims, 10 Drawing Sheets

PYRIDINE BASED IONIC FLUORIDE FOR CATALYZING INDOLE AND TETRAZOLE FORMATION

STATEMENT REGARDING PRIOR DISCLOSURE BY THE INVENTORS

Aspects of this technology are described in an article "N,N-Dimethylpyridin-4-amine (DMAP) based ionic liquids: evaluation of physical properties via molecular dynamics simulations and application as a catalyst for Fisher indole and 1H-tetrazole synthesis" published in RSC Advances, 2017, 7, 34197-34207, on Jul. 7, 2017, which is incorporated herein by reference in its entirety.

BACKGROUND OF THE INVENTION

Technical Field

The present invention relates to pyridine based ionic liquids having fluoride counter anions and methods of synthesizing indoles/indolenines and tetrazoles with the pyridine based ionic liquids.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Although the concept of ionic liquids (ILs) has been around for more than a hundred years, a sudden surge in the interest of applications of ILs has been witnessed in both academia and industry in the past three decades [T. Welton, Chem. Rev., 99 (1999) 2071-2084; J. P. Hallett, T. Welton, Chem. Rev., 111 (2011) 3508-3576; N. V. Plechkova, K. R. Seddon, Chem. Soc. Rev., 37 (2008) 123-150; and R. D. Rogers, K. R. Seddon, S. Volkov, Green industrial applications of ionic liquids, Springer Science & Business Media, 2012]. Traditionally, ILs are defined as salts being made up of positively and negatively charged ions that are liquid at temperatures typically below 100° C. [P. Wasserscheid, T. Welton, Ionic liquids in synthesis, John Wiley & Sons, 2008]. However, there is no strict adherence to this criteria of IL being liquid at temperature below 100° C., and many high temperature ILs have been reported [V. G. Rao, C. Banerjee, S. Ghosh, S. Mandal, J. Kuchlyan, N. Sarkar, J. Phys. Chem. B, 117 (2013) 7472-7480].

ILs are widely regarded as "designer liquids" because their individual cationic or anionic moiety can be independently selected according to particular applications. Consequently, physiochemical properties of ILs can be tailored as desired, which allows flexibility in the design and applications of ILs [H. Niedermeyer, J. P. Hallett, I. J. Villar-Garcia, P. A. Hunt, T. Welton, Chem. Soc. Rev., 41 (2012) 7780-7802]. The use of ILs as catalysts for organic syntheses has increased recently. Other properties of ILs such as low volatility, high thermal stability, and ease of recycling further increase their appeal [M. Freemantle, An introduction to ionic liquids, Royal Society of Chemistry, 2009]. Nitrogen containing cationic scaffolds, e.g. pyridine and imidazole with various counter ions have been widely employed for catalyzing various organic reactions [R. L. Vekariya, J. Mol. Liq., 227 (2016) 44-60, incorporated herein by reference in its entirety]. However, imidazole's inert nature [X. Chen, A. Ying, DBU derived ionic liquids and their application in organic synthetic reactions, INTECH Open Access Publisher, 2011, incorporated herein by reference in its entirety] and extreme toxicity, as well as pyridine's volatility impedes their utilization in organic syntheses. It is therefore necessary to design and develop new ionic liquids with less toxic cations. N,N-Dimethylpyridin-4-amine (DMAP), is a pyridine based non-volatile, crystalline reagent. DMAP has been extensively used as a catalyst in organic syntheses, especially in coupling reactions, such as esterification, amide formation and for attaching protecting groups (i.e. TBS, Boc) [G. Sabitha, N. M. Reddy, M. N. Prasad, J. S. Yadav, Helv. Chim. Acta, 92 (2009) 967-976; and G. Kumaraswamy, A. Pitchaiah, Helv. Chim. Acta, 94 (2011) 1543-1550, each incorporated herein by reference in their entirety].

In view of the forgoing, one objective of the present invention is to provide a pyridine based ionic liquid having a fluoride counter anion which is effective for catalyzing organic reactions including Fischer indole synthesis and click reaction. Another objective of the present disclosure is to provide methods of employing the ionic liquid as a catalyst to prepare indoles/indolenines and tetrazoles.

BRIEF SUMMARY OF THE INVENTION

According to a first aspect, the present disclosure relates to an ionic liquid of formula (I)

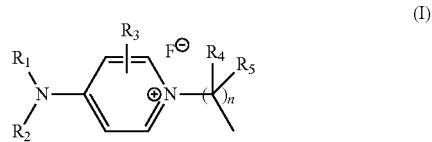

or a solvate thereof, a tautomer thereof, a stereoisomer thereof, or a mixture thereof wherein (i) $R_1$ and $R_2$ are independently selected from the group consisting of an optionally substituted alkyl, an optionally substituted cycloalkyl, an optionally substituted arylalkyl, and an optionally substituted aryl, (ii) $R_3$ is selected from the group consisting of a hydrogen, an optionally substituted alkyl, an optionally substituted cycloalkyl, an optionally substituted arylalkyl, an optionally substituted aryl, an optionally substituted alkoxy, an optionally substituted alkanoyl, an optionally substituted aroyl, a halogen, a nitro, and a cyano, (iii) $R_4$ and $R_5$ are independently selected from the group consisting of a hydrogen, an optionally substituted alkyl, an optionally substituted cycloalkyl, an optionally substituted arylalkyl, and an optionally substituted aryl, and (iv) n is an integer in a range of 0-15.

In one embodiment, $R_1$ and $R_2$ are independently an optionally substituted alkyl, and $R_3$ is a hydrogen.

In one embodiment, n is an integer in a range of 1-15, and wherein $R_4$ and $R_5$ are a hydrogen.

In one embodiment, n is an integer in a range of 2-8.

In one embodiment, $R_1$ and $R_2$ are a methyl.

In one embodiment, the ionic liquid is at least one selected from the group consisting of (II)

[Structure: dimethylamino-pyridinium with N-(CH₂)₄-ethyl group, F⁻ counterion]

and (III)

[Structure: dimethylamino-pyridinium with N-(CH₂)₆-ethyl group, F⁻ counterion]

According to a second aspect, the present disclosure relates to a method of synthesizing the ionic liquid of the first aspect. The method includes reacting a pyridine compound of formula (IV)

(IV)

[Structure: pyridine with R₁R₂N- substituent and R₃ substituent]

or a salt thereof, a solvate thereof, a stereoisomer thereof, or a mixture thereof with an alkyl halide of formula (V)

(V)

[Structure: X-C(R₄)(R₅)-(CH₂)ₙ-CH₃]

or a salt thereof, a solvate thereof, a stereoisomer thereof, or a mixture thereof to obtain a N-alkylated pyridinium halide, and treating the N-alkylated pyridinium halide with a fluoride salt, thereby forming the ionic liquid of formula (I) wherein (i) $R_1$ and $R_2$ are independently selected from the group consisting of an optionally substituted alkyl, an optionally substituted cycloalkyl, an optionally substituted arylalkyl, and an optionally substituted aryl, (ii) $R_3$ is selected from the group consisting of a hydrogen, an optionally substituted alkyl, an optionally substituted cycloalkyl, an optionally substituted arylalkyl, an optionally substituted aryl, an optionally substituted alkoxy, an optionally substituted alkanoyl, an optionally substituted aroyl, a halogen, a nitro, and a cyano, (iii) $R_4$ and $R_5$ are independently selected from the group consisting of a hydrogen, an optionally substituted alkyl, an optionally substituted cycloalkyl, an optionally substituted arylalkyl, and an optionally substituted aryl; (iv) X is a chloride, a bromide, or an iodide; and (v) n is an integer in a range of 0-15.

In one embodiment, a molar ratio of the pyridine compound of formula (IV) to the alkyl halide of formula (V) is in a range of 1:2 to 2:1.

In one embodiment, the fluoride salt is at least one selected from the group consisting of transition metal fluorides, alkali metal fluorides, ammonium fluoride, and hydrogen fluoride.

In one embodiment, the fluoride salt is silver fluoride.

According to a third aspect, the present disclosure relates to a method of synthesizing an indole or indolenine. The method involves reacting an aryl hydrazine with an alkyl ketone or an alkyl aldehyde in the presence of the ionic liquid of the first aspect, thereby forming the indole or indolenine.

In one embodiment, the ionic liquid is (II)

[Structure: dimethylamino-pyridinium with N-(CH₂)₄-ethyl group, F⁻ counterion]

or (III)

[Structure: dimethylamino-pyridinium with N-(CH₂)₆-ethyl group, F⁻ counterion]

In one embodiment, a molar ratio of the aryl hydrazine to the alkyl ketone or the alkyl aldehyde is in a range of 1:2 to 2:1, and the ionic liquid is present in an amount of 5 mol % to 40 mol % relative to moles of the aryl hydrazine.

In one embodiment, the reacting is conducted at a temperature in the range of 60° C. to 120° C.

In one embodiment, the indole and indolenine is at least one selected from the group consisting of (6a)

[Structure: tetrahydrocarbazole]

(6b)

[Structure: methoxy-substituted tetrahydrocarbazole, OMe]

(6c)

[Structure: fluoro-substituted tetrahydrocarbazole, F]

(6d)

[Structure: methyl, methoxy-substituted tetrahydrocarbazole, OMe]

(6e)

[Structure: methyl, chloro-substituted indolenine, Cl]

(6f)

[Structure: cyano-substituted tetrahydrocarbazole, CN]

-continued

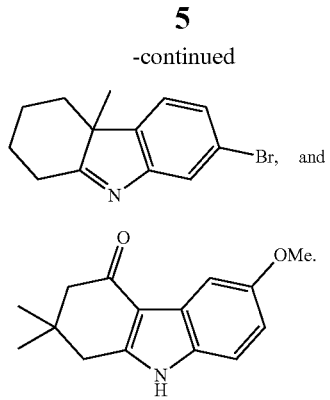
(6g)

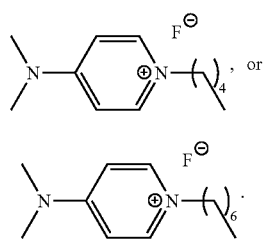
(6h)

According to a fourth aspect, the present disclosure relates to a method of synthesizing a tetrazole. The method involves reacting a nitrile with an azide in the presence of the ionic liquid of the first aspect, thereby forming the tetrazole.

In one embodiment, the ionic liquid is

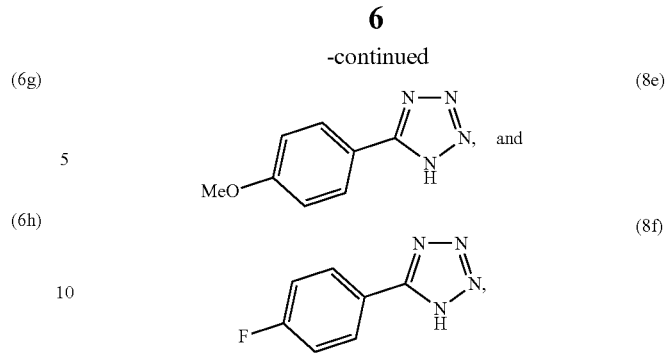
(II)

(III)

In one embodiment, a molar ratio of the nitrile to the azide is in a range of 1:2 to 1:6, and the ionic liquid is present in an amount of 10 mol % to 50 mol % relative to moles of the nitrile.

In one embodiment, the reacting is conducted at a temperature in the range of 80° C. to 150° C.

In one embodiment, the tetrazole is at least one selected from the group consisting of

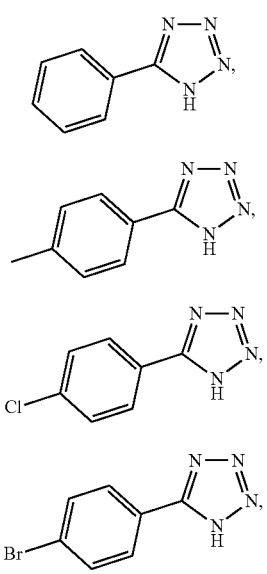
(8a)

(8b)

(8c)

(8d)

(8e)

(8f)

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
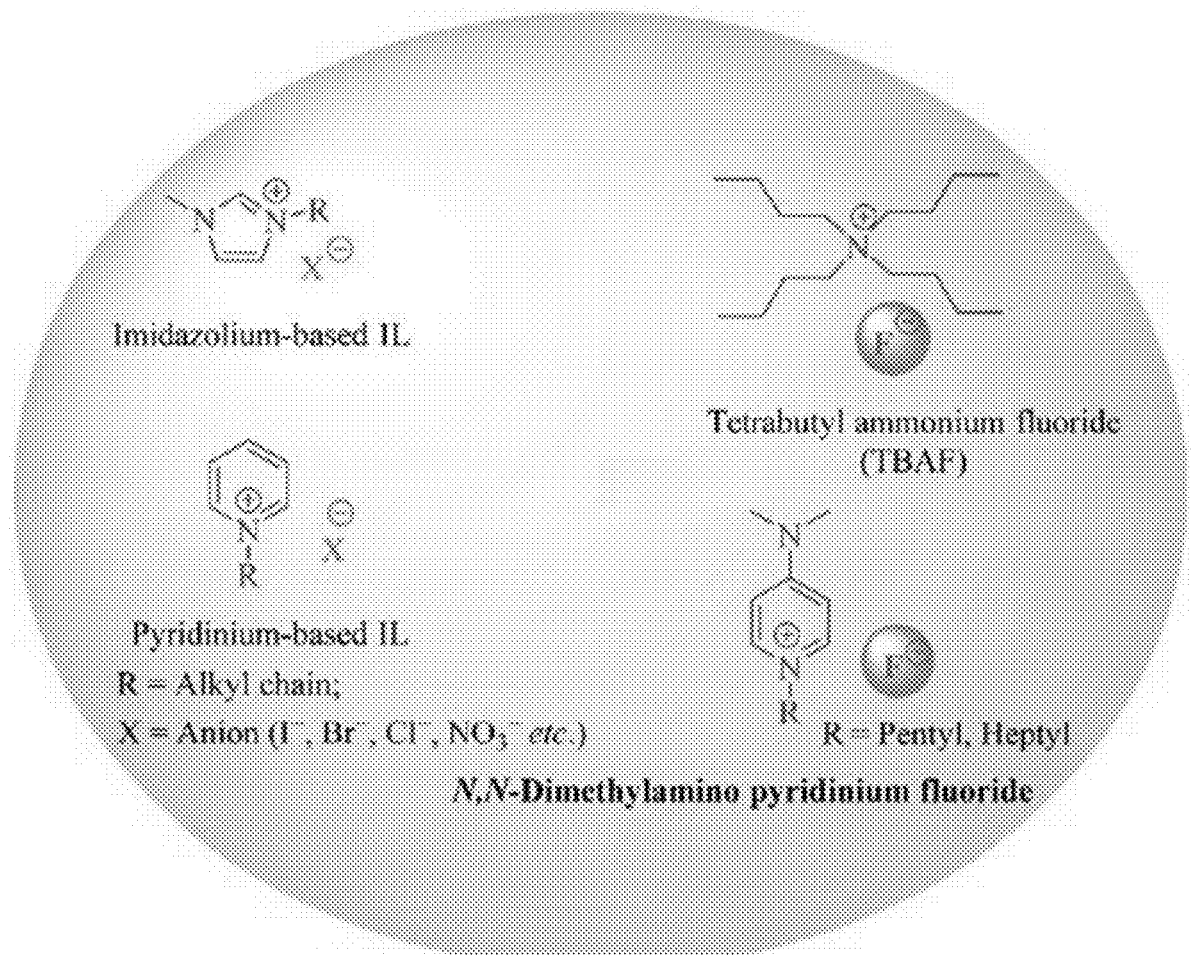
FIG. 1 shows structures of imidazolium fluoride, pyridinium fluoride, tetrabutyl ammonium fluoride, and N,N-dimethylamino pyridinium fluoride.

Embodiments of the present disclosure will now be described more fully hereinafter with reference to the accompanying drawings, in which some, but not all embodiments of the disclosure are shown. The present disclosure will be better understood with reference to the following definitions.

Unless otherwise specified, "a" or "an" means "one or more". Within the description of this disclosure, where a numerical limit or range is stated, the endpoints are included unless stated otherwise. Also, all values and subranges within a numerical limit or range are specifically included as if explicitly written out.

As used herein, the terms "compound", "product" and "catalyst" are used interchangeably, and are intended to refer to a chemical entity, whether in the solid, liquid or gaseous phase, and whether in a crude mixture or purified and isolated. An "ionic liquid" generally refers to a liquid that are comprised entirely of ions. As used herein, an ionic liquid may have a homogeneous composition consisting of one cationic species and one anionic species or a heterogeneous composition comprising more than one species of cation and/or more than one species of anion.

As used herein, the term "solvate" refers to a physical association of a compound of this disclosure with one or more solvent molecules, whether organic or inorganic. This physical association includes hydrogen bonding. In certain instances, the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. Solvate encompasses both solution phase and isolable solvates. Exemplary solvents include, but are not limited to, water, methanol, ethanol, n-propanol, isopropanol, n-butanol, isobutanol, tert-butanol, ethyl acetate and other lower alkanols, glycerine, acetone, dichloromethane (DCM), dimethyl sulfoxide (DMSO), dimethyl acetate (DMA), dimethylformamide (DMF), isopropyl ether, acetonitrile, toluene, N-methylpyrrolidone (NMP), tetrahydrofuran (THF), tetrahydropyran, other cyclic mono-, di- and tri-ethers, polyalkylene glycols (e.g. polyethylene glycol, polypropylene glycol, propylene glycol), and mixtures thereof in suitable proportions. Exemplary solvates include, but are not limited to, hydrates, ethanolates, methanolates, isopropanolates and mixtures thereof. Methods of solvation are generally known to those skilled in the art.

As used herein, the term "tautomer" refers to constitutional isomers of organic compounds that readily convert by tautomerization or tautomerism. The interconversion commonly results in the formal migration of a hydrogen atom or proton, accompanied by a switch of a single bond and adjacent double bond. Tautomerism is a special case of structural isomerism, and because of the rapid interconversion, tautomers are generally considered to be the same chemical compound. In solutions in which tautomerization is possible, a chemical equilibrium of the tautomers will be reached. The exact ratio of the tautomers depends on several factors including, but not limited to, temperature, solvent and pH. Exemplary common tautomeric pairs include, but are not limited to, ketone and enol, enamine and imine, ketene and ynol, nitroso and oxime, amide and imidic acid, lactam and lactim (an amide and imidic tautomerism in heterocyclic rings), and open-chain and cyclic forms of an acetal or hemiacetal (e.g., in reducing sugars).

As used herein, the term "stereoisomer" refers to isomeric molecules that have the same molecular formula and sequence of bonded atoms (i.e. constitution), but differ in the three-dimensional orientations of their atoms in space. This contrasts with structural isomers, which share the same molecular formula, but the bond connection of their order differs. By definition, molecules that are stereoisomers of each other represent the same structural isomer. Enantiomers are two stereoisomers that are related to each other by reflection, they are non-superimposable mirror images. Every stereogenic center in one has the opposite configuration in the other. Two compounds that are enantiomers of each other have the same physical properties, except for the direction in which they rotate polarized light and how they interact with different optical isomers of other compounds. Diastereomers are stereoisomers not related through a reflection operation, they are not mirror images of each other. These include meso compounds, cis- and trans- (E- and Z-) isomers, and non-enantiomeric optical isomers. Diastereomers seldom have the same physical properties. In terms of the present disclosure, stereoisomers may refer to enantiomers, diastereomers, or both.

Conformers, rotamers, or conformational isomerism refers to a form of isomerism that describes the phenomenon of molecules with the same structural formula but with different shapes due to rotations around one or more bonds. Different conformations can have different energies, can usually interconvert, and are very rarely isolatable. There are some molecules that can be isolated in several conformations. Atropisomers are stereoisomers resulting from hindered rotation about single bonds where the steric strain barrier to rotation is high enough to allow for the isolation of the conformers. In terms of the present disclosure, stereoisomers may refer to conformers, atropisomers, or both.

In terms of the present disclosure, stereoisomers of the double bonds, ring systems, stereogenic centers, and the like can all be present in the compounds, and all such stable isomers are contemplated in the present disclosure. Cis- and trans- (or E- and Z-) stereoisomers of the compounds of the present disclosure wherein rotation around the double bond is restricted, keeping the substituents fixed relative to each other, are described and may be isolated as a mixture of isomers or as separated isomeric forms. S- and R- (or L- and D-) stereoisomers of the compounds of the present disclosure are described and may be isolated as a mixture of isomers or as separated isomeric forms. All processes or methods used to prepare compounds of the present disclosure and intermediates made therein are considered to be part of the present disclosure. When stereoisomeric products are prepared, they may be separated by conventional methods, for example, by chromatography, fractional crystallization, or use of a chiral agent.

The present disclosure is further intended to include all isotopes of atoms occurring in the present compounds. Isotopes include those atoms having the same atomic number but different mass numbers. By way of general example, and without limitation, isotopes of hydrogen include deuterium and tritium, isotopes of carbon include $^{13}$C and $^{14}$C, isotopes of nitrogen include $^{15}$N, isotopes of oxygen include $^{17}$O and $^{18}$O, and isotopes of fluorine include $^{18}$F. Isotopically labeled compounds of the disclosure can generally be prepared by conventional techniques known to those skilled in the art or by processes and methods analogous to those described herein, using an appropriate isotopically labeled reagent in place of the non-labeled reagent otherwise employed.

As used herein, the term "substituted" refers to at least one hydrogen atom that is replaced with a non-hydrogen group, provided that normal valencies are maintained and that the substitution results in a stable compound. When a substituent is noted as "optionally substituted", the substituents are selected from the exemplary group including, but not limited to, halo, hydroxyl, alkoxy, oxo, alkanoyl, aryloxy, alkanoyloxy, amino, alkylamino, arylamino, arylalkylamino, disubstituted amines (e.g. in which the two amino substituents are selected from the exemplary group including, but not limited to, alkyl, aryl or arylalkyl), alkanylamino, aroylamino, aralkanoylamino, substituted alkanoylamino, substituted arylamino, aubstituted aralkanoylamino, thiol, alkylthio, arylthio, arylalkylthio, alkylthiono, arylthiono, aryalkylthiono, alkylsulfonyl, arylsulfonyl, arylalkylsulfonyl, sulfonamide (e.g. —SO$_2$NH$_2$), substituted sulfonamide, nitro, cyano, carboxy, carbamyl (e.g. —CONH$_2$), substituted carbamyl (e.g. —CONHalkyl, —CONHaryl, —CONHarylalkyl or cases where there are two substituents on one nitrogen from alkyl, aryl, or alkylalkyl), alkoxycarbonyl, aryl, substituted aryl, guanidine, heterocyclyl (e.g. indolyl, imidazoyl, furyl, thienyl, thiazolyl, pyrrolidyl, pyridyl, pyrimidiyl, pyrrolidinyl, piperidinyl, morpholinyl, piperazinyl, homopiperazinyl and the like), substituted heterocyclyl and mixtures thereof and the like. The substituents may themselves be optionally substituted, and may be either unprotected, or protected as necessary, as known to those skilled in the art, for example, as taught in Greene, et al., "Protective Groups in Organic Synthesis", John Wiley and Sons, Second Edition, 1991, hereby incorporated by reference in its entirety.

As used herein, the term "alkyl" unless otherwise specified refers to both branched and straight chain saturated aliphatic primary, secondary, and/or tertiary hydrocarbons of typically $C_1$ to $C_{20}$, preferably $C_2$-$C_{15}$, more preferably $C_3$-$C_8$, for example $C_1$, $C_2$, $C_3$, $C_4$, $C_5$, $C_6$, $C_7$, $C_8$, $C_9$, $C_{10}$, $C_{11}$, $C_{12}$, and specifically includes, but is not limited to, methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, 2,3-dimethylbutyl, 2-ethylhexyl, heptyl, octyl, nonyl, 3,7-dimethyloctyl, decyl, undecyl, dodecyl, tridecyl, 2-propylheptyl, tetradecyl, pentadecyl, hexadecyl, heptadecyl, octadecyl, nonadecyl, and eicosyl. As used herein, the term optionally includes substituted alkyl groups. Exemplary moieties with which the alkyl group can be substituted may be selected from the group including, but not limited to, hydroxyl, amino, alkylamino, arylamino, alkoxy, aryloxy, nitro, cyano, sulfonic acid, sulfate, phosphonic acid, phosphate, halo, or phosphonate or mixtures thereof. The substituted moiety may be either protected or unprotected as necessary, and as known to those skilled in the art.

As used herein, the term "cycloalkyl" refers to cyclized alkyl groups. Exemplary cycloalkyl groups include, but are not limited to, cyclopropyl, cyclobutyl, cyclopentyl, cyclohexyl, norbornyl, and adamantyl. Branched cycloalkyl groups such as exemplary 1-methylcyclopropyl and 2-methylcyclopropyl groups are included in the definition of cycloalkyl as used in the present disclosure.

The term "arylalkyl", as used herein, refers to a straight or branched chain alkyl moiety having 1 to 8 carbon atoms that is substituted by an aryl group as defined herein, and includes, but is not limited to, benzyl, phenethyl, 2-methylbenzyl, 3-methylbenzyl, 4-methylbenzyl, 2,4-dimethylbenzyl, 2-(4-ethylphenyl)ethyl, 3-(3-propylphenyl)propyl, and the like.

As used herein, the term "aryl" unless otherwise specified refers to functional groups or substituents derived from an aromatic ring including, but not limited to, phenyl, biphenyl, napthyl, thienyl, and indolyl. As used herein, the term optionally includes both substituted and unsubstituted moieties. Exemplary moieties with which the aryl group can be substituted may be selected from the group including, but not limited to, hydroxyl, amino, alkylamino, arylamino, alkoxy, aryloxy, nitro, cyano, halide, sulfonic acid, sulfate, phosphonic acid, phosphate or phosphonate or mixtures thereof. The substituted moiety may be either protected or unprotected as necessary, and as known to those skilled in the art.

The term "alkoxy" refers to a straight or branched chain alkoxy including, but not limited to, methoxy, ethoxy, propoxy, isopropoxy, butoxy, isobutoxy, secondary butoxy, tertiary butoxy, pentoxy, isopentoxy, hexyloxy, heptyloxy, octyloxy, nonyloxy, and decyloxy.

The term "alkanoyl" refers to an alkyl group of specified number of carbon atoms that is bound to an oxygen atom through a double bond. Exemplary alkanoyl groups include, but are not limited to, formyl, acetyl, propanoyl, butyryl, and hexanoyl.

The term "aroyl" as used in this disclosure refers to an aromatic carboxylic acyl group includes, for example, benzoyl, 1-naphthoyl, and 2-naphthoyl.

The term "halogen", as used herein, means fluoro, chloro, bromo and iodo.

The term "heterocyclyl" refers to a saturated or unsaturated organic group that contains one or more rings in which one or more ring members is a heteroatom, preferably a nitrogen, sulfur or oxygen heteroatom, such as, for example, thiacyclopentadienyl, thiaindenyl, thianthrenyl, oxacyclopentadienyl, oxaindenyl, isobenzylfuranyl, pyranyl, azacyclopentadienyl, pyridinyl, pyrazinyl, pyrimidinyl, pyridazinyl, indolinyl, quinolinyl, isoquinolinyl, phthalazinyl, cinnolinyl, azafluorenyl, phenanthrolinyl, phenazinyl, phenothiazinyl, phenarsazinyl, isothiazolyl, isoxazolyl, phenoxazinyl, pyrrolidinyl, pyrimadinyl, imidazolidinyl, piperidinyl, piperizinyl, oxathiaanthracenyl, isoxazolyl, oxaazaanthracenyl, isothiazolyl, morpholinyl, and which may, optionally, be substituted at one or more positions with other moieties, such as, for example, any of the possible substituents described above.

According to a first aspect, the present disclosure relates to an ionic liquid of formula (I)

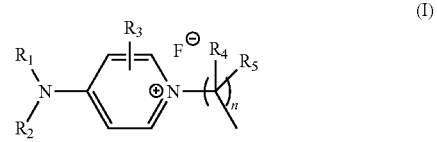

or a solvate thereof, a tautomer thereof, a stereoisomer thereof, or a mixture thereof.

$R_1$ and $R_2$ are independently selected from the group consisting of an optionally substituted alkyl, an optionally substituted cycloalkyl, an optionally substituted arylalkyl, and an optionally substituted aryl. In some embodiments, $R_1$ and $R_2$ are independently an optionally substituted alkyl. Preferably, $R_1$ and $R_2$ are a methyl.

$R_3$ is selected from the group consisting of a hydrogen, an optionally substituted alkyl, an optionally substituted cycloalkyl, an optionally substituted arylalkyl, an optionally substituted aryl, an optionally substituted alkoxy, an optionally substituted alkanoyl, an optionally substituted aroyl, a halogen, a nitro, and a cyano. In preferred embodiments, $R_3$ is a hydrogen.

$R_4$ and $R_5$ are independently selected from the group consisting of a hydrogen, an optionally substituted alkyl, an optionally substituted cycloalkyl, an optionally substituted arylalkyl, and an optionally substituted aryl. In preferred embodiments, $R_4$ and $R_5$ are a hydrogen.

As used herein, the value of n denotes an alkyl chain of —C($R_4$)($R_5$)— groups. In a preferred embodiment, n is an integer in a range of 0-15, preferably 1-14, preferably 2-13, preferably 3-12, preferably 4-11, preferably 5-10, preferably 6-9, preferably 7-8.

In one or more embodiments, $R_1$ and $R_2$ are independently an optionally substituted alkyl, and $R_3$ is a hydrogen. In some embodiments, $R_1$ and $R_2$ are independently a linear (unsubstituted) alkyl, e.g. methyl, ethyl, n-propyl, n-butyl, n-pentyl, n-hexyl, and $R_3$ is a hydrogen. In a preferred embodiment, $R_1$ and $R_2$ are a methyl, and $R_3$ is a hydrogen.

In one or more embodiments, n is an integer in a range of 1-15, preferably 2-14, preferably 3-13, preferably 4-12, preferably 5-11, preferably 6-10, preferably 7-9, and $R_4$ and $R_5$ are independently selected from the group consisting of a hydrogen, an optionally substituted alkyl, an optionally substituted cycloalkyl, an optionally substituted arylalkyl, and an optionally substituted aryl. In a preferred embodiment, n is an integer in a range of 1-15, preferably 2-14, preferably 3-13, preferably 4-12, preferably 5-11, preferably 6-10, preferably 7-9, and $R_4$ and $R_5$ are each a hydrogen.

In one embodiment, the ionic liquid is at least one selected from the group consisting of

 (II) , and

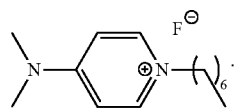 (III) .

The present disclosure is intended to include an ionic liquid of formula (I) where adjacent $R_1$ and $R_2$ groups together form a cyclic ring with the nitrogen atom to which they are attached, thereby forming a 3-membered, 4-membered, 5-membered, 6-membered, 7-membered, or 8-membered ring. The —N($R_1$)($R_2$) of formula (I) may form a cyclic or heterocyclic ring, for example, of the following structures:

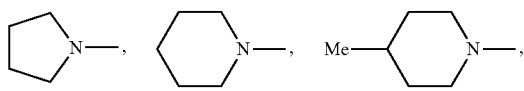

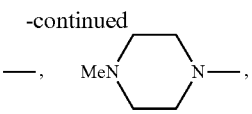

as well as substituted variants of such cyclic rings.

According to a second aspect, the present disclosure relates to a method of synthesizing the ionic liquid of the first aspect. The method includes reacting a pyridine compound of formula (IV)

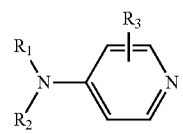 (IV)

or a salt thereof, a solvate thereof, a stereoisomer thereof, or a mixture thereof with an alkyl halide of formula (V)

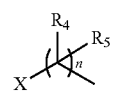 (V)

or a salt thereof, a solvate thereof, a stereoisomer thereof, or a mixture thereof to obtain a N-alkylated pyridinium halide, and treating the N-alkylated pyridinium halide with a fluoride salt, thereby forming the ionic liquid of formula (I) wherein (i) $R_1$ and $R_2$ are independently selected from the group consisting of an optionally substituted alkyl, an optionally substituted cycloalkyl, an optionally substituted arylalkyl, and an optionally substituted aryl, (ii) $R_3$ is selected from the group consisting of a hydrogen, an optionally substituted alkyl, an optionally substituted cycloalkyl, an optionally substituted arylalkyl, an optionally substituted aryl, an optionally substituted alkoxy, an optionally substituted alkanoyl, an optionally substituted aroyl, a halogen, a nitro, and a cyano, (iii) $R_4$ and $R_5$ are independently selected from the group consisting of a hydrogen, an optionally substituted alkyl, an optionally substituted cycloalkyl, an optionally substituted arylalkyl, and an optionally substituted aryl; (iv) X is a chloride, a bromide, or an iodide, preferably X is a bromide, and (v) n is an integer in a range of 0-15, 1-14, 2-13, 3-12, 4-11, 5-10, 6-9, or 7-8.

In a preferred embodiment, reacting the pyridine compound of formula (IV) and the alkyl halide of formula (V) to obtain the N-alkylated pyridinium halide is performed in a non-polar solvent, preferably in toluene. Exemplary non-polar solvents that may be used in addition to, or in lieu of toluene include, but are not limited to, benzene, 1,4-dioxane, cyclohexane, hexane, pentane, cyclopentane, chloroform, dichloromethane, diethyl ether, and mixtures thereof. It is equally envisaged that the reaction may be adapted to be performed in a polar aprotic solvent such as tetrahydrofuran, ethyl acetate, acetonitrile, dimethylformamide, dimethyl sulfoxide, and propylene carbonate. In a preferred embodiment, the reaction is performed at a concentration of the pyridine compound in the range of 0.1-200 M, preferably 0.5-100 M, preferably 1-50 M, preferably 2-25 M, preferably 5-15 M. In a preferred embodiment, the reaction is performed under mechanical stirring, preferably a magnetic stirrer at a temperature of up to 160° C., preferably 10-150°

C., preferably 20-130° C., preferably 40-120° C., preferably 60-110° C., preferably 70-100° C. and has a reaction time of up to 24 hours, preferably 1-20 hours, preferably 2-16 hours, preferably 4-12 hours, preferably 6-10 hours. In a preferred embodiment, a molar ratio of the pyridine compound of formula (IV) to the alkyl halide of formula (V) is in the range of 1:3 to 3:1, preferably 1:2 to 2:1, preferably 2:3 to 3:2, or about 1:1. In a preferred embodiment, the N-alkylated pyridinium halide is collected as an oil that may be separated and washed in toluene, and then dried. In one embodiment, the oil may be dried under vacuum at 20-100° C., preferably 40-80° C. until a constant weight is achieved. In a preferred embodiment, the reaction has a product yield of at least 50%, preferably at least 60%, preferably at least 65%, preferably at least 70%, preferably at least 75%, preferably at least 80%. As defined herein, the pyridine compound of formula (IV) may be considered as a limiting reagent when the molar ratio of the pyridine compound of formula (IV) to the alkyl halide of formula (V) is less than or equals 1, and the alkyl halide of formula (V) may be considered as the limiting reagent when the molar ratio of the pyridine compound of formula (IV) to the alkyl halide of formula (V) is greater than or equals 1. The product yield is calculated as (mole of product/mole of the limiting reagent)×100%.

the fluoride salt is at least one selected from the group consisting of transition metal fluorides, alkali metal fluorides, ammonium fluoride, and hydrogen fluoride.

In one or more embodiments, the fluoride salt used herein is at least one selected from the group consisting of transition metal fluorides (e.g. silver fluoride), alkali metal fluorides, ammonium fluoride, and hydrogen fluoride. Non-limiting examples of alkali metal fluorides include sodium fluoride, potassium fluoride, and cesium fluoride. In a preferred embodiment, the fluoride salt is silver fluoride.

In a preferred embodiment, treating the N-alkylated pyridinium halide with the fluoride salt to form the ionic liquid of formula (I) is conducted in polar protic solvent, preferably in water. Exemplary polar protic solvents that may be used in addition to, or in lieu of water include, but are not limited to, methanol, ethanol, n-propanol, isopropyl alcohol, n-butanol, and mixtures thereof. In a preferred embodiment, the reaction is performed at a concentration of the N-alkylated pyridinium halide in the range of 0.1-100 M, preferably 0.5-50 M, preferably 1-25 M, preferably 2.5-20 M, preferably 5-10 M. In a preferred embodiment, the reaction is performed under mechanical stirring, preferably a magnetic stirrer at a temperature of up to 80° C., preferably 5-60° C., preferably 10-50° C., preferably 15-40° C., preferably 20-35° C., preferably 25-30° C. and has a reaction time of up to 24 hours, preferably 1-20 hours, preferably 2-16 hours, preferably 4-12 hours, preferably 6-10 hours. In a preferred embodiment, a molar ratio of the N-alkylated pyridinium halide to the fluoride salt is in the range of 1:8 to 1:1, preferably 1:7 to 1:1.5, preferably 1:6 to 1:2, preferably 1:5 to 1:3. In a preferred embodiment, the ionic liquid is collected as an oil that may be separated and washed in toluene and/or hexane and then dried. In one embodiment, the oil may be dried under vacuum at 20-100° C., preferably 40-80° C. until a constant weight is achieved. In a preferred embodiment, the reaction has a product yield of at least 60%, preferably at least 65%, preferably at least 70%, preferably at least 75%, preferably at least 80%, preferably at least 85%, preferably at least 90%. The product yield is calculated as (mole of product/mole of the N-alkylated pyridinium halide)×100%.

Indole is a bicyclic hetero-aromatic scaffold which serves as an important structural component in many medicinally important compounds such as serotonin, melatonin, and alosetron etc. [R. Sundberg, The chemistry of indoles, Academic Press, New York and London, 2012, incorporated herein by reference in its entirety]. A number of synthetic protocols have been reported for the preparation of indole scaffold. However, Fischer indole synthesis remains one of the most popular and important methods. A typical Fischer indole method involves coupling of a ketone with an arylhydrazine to from an arylhydrazone, and subsequent releasing of ammonia via a [3,3]-sigmatropic arrangement under acidic conditions to furnish the indole ring. Since Fischer's discovery, a range of different catalysts such as protic acids ($H_2SO_4$, polyphosphoric acid, HCl, AcOH), Lewis acids ($TiCl_4$, $ZnCl_2$, $PCl_3$), and imidazole [D.-Q. Xu, J. Wu, S.-P. Luo, J.-X. Zhang, J.-Y. Wu, X.-H. Du, Z.-Y. Xu, Green Chem., 11 (2009) 1239-1246, incorporated herein by reference in its entirety] or pyridine [G. L. Rebeiro, B. M. Khadilkar, Synthesis, 2001 (2001) 0370-0372, incorporated herein by reference in its entirety] based ionic liquids, have been tested to catalyze the Fischer indole reaction. Recently low melting mixtures, also called deep eutectic solvents (DES), have also been used to carry out indole formation [S. Gore, S. Baskaran, B. Konig, Org. Lett., 14 (2012) 4568-4571, incorporated herein by reference in its entirety]. In these reactions, large quantities of low melting mixture (DES), i.e. up to a gram per one mmol scale reaction are required, complicating reaction purification.

According to a third aspect, the present disclosure relates to a method of synthesizing an indole or an indolenine. The method involves reacting an aryl hydrazine with an alkyl ketone or an alkyl aldehyde in the presence of the ionic liquid of the first aspect thereby forming the indole or the indolenine.

In one or more embodiments, the ionic liquid is present in an amount of 5 mol % to 40 mol %, preferably 10 mol % to 35 mol %, preferably 15 mol % to 30 mol %, preferably 18 mol % to 25 mol %, or about 20 mol % relative to moles of the aryl hydrazine. Although an ionic liquid concentration higher than 40 mol % (e.g. up to 50 mol %, 60 mol %, 80 mol %, 100 mol % relative to moles of the aryl hydrazine) may be used and the method may still proceed as intended. In a preferred embodiment, reacting the aryl hydrazine with the alkyl ketone or the alkyl aldehyde in the presence of the ionic liquid is conducted in a polar protic solvent, preferably in ethanol. Exemplary polar protic solvents that may be used in addition to, or in lieu of ethanol include, but are not limited to, methanol, n-propanol, isopropyl alcohol, n-butanol, and mixtures thereof. It is equally envisaged that the reaction may be adapted to be performed in a polar aprotic solvent such as dimethylformamide, tetrahydrofuran, ethyl acetate, acetone, acetonitrile, and dimethyl sulfoxide. In certain embodiments, reacting the aryl hydrazine with the alkyl ketone or the alkyl aldehyde in the presence of the ionic liquid is conducted without a solvent. In a preferred embodiment, the reaction is performed at a concentration of the aryl hydrazine in the range of 0.01-100 M, preferably 0.05-50 M, preferably 0.1-25 M, preferably 0.3-10 M, preferably 1-5 M. In a preferred embodiment, a molar ratio of the aryl hydrazine to the alkyl ketone or the alkyl aldehyde is in a range of 1:3 to 3:1, preferably 1:2 to 2:1, preferably 2:3 to 3:2, or about 1:1. In a preferred embodiment, the reaction is performed at a concentration of the ionic liquid in the range of 0.1-10,000 mM, preferably 1-1,000 mM, preferably 10-100 mM, preferably 20-80 mM, preferably 40-60 mM. In a preferred embodiment, the aforementioned reaction is performed under agitation at a temperature of up to 150° C., preferably 20-120° C., preferably 40-90° C., preferably 50-80° C., preferably 60-70° C. and has a reaction time of up to 120 hours, preferably 0.1-60 hours, preferably 0.5-48 hours, preferably 1-36 hours, preferably 2-24 hours. An external heat source, such as a water bath or an oil bath, an oven, microwave, or a heating mantle, may be employed to heat the reaction mixture. The reaction mixture may be agitated throughout the duration of the reaction by employing a rotary shaker, a magnetic stirrer, or an overhead stirrer. In another embodiment, the reaction mixture is left to stand (i.e. not agitated). In one embodiment, the reaction mixture is stirred by a magnetic stirrer at a speed of at least 300 rpm, preferably at least 500 rpm, preferably at least 700 rpm, preferably at least 900 rpm. In one embodiment, the reaction mixture is sonicated in an ultrasonic bath or with an ultrasonic probe.

In some embodiments, prior to reacting, the method further comprises an adding step where the aryl hydrazine is added to the solvent, followed by the alkyl ketone or the alkyl aldehyde and the ionic liquid. In another embodiment, the ionic liquid is first dissolved in the solvent to form an ionic liquid solution, which is then added to a mixture of the aryl hydrazine and the alkyl ketone or the alkyl aldehyde. Preferably, the adding and the reacting steps are performed in an inert atmosphere provided by an inert gas such as $N_2$, Ar, He, or mixtures thereof. For example, the inert gas may be bubbled in the reaction mixture for at least 0.5 hour, 1 hour, or at least 2 hours before and/or during the reaction.

The progress of the aforementioned reaction may be monitored by methods known to those skilled in the art, such as thin layer chromatography, gas chromatography, nuclear magnetic resonance, infrared spectroscopy, and high pressure liquid chromatography combined with ultraviolet detection or mass spectroscopy. Preferably, thin layer chromatography is used.

The indoles or the indolenines formed by the method disclosed herein are isolated and purified by methods known to those skilled in the art, such as filtration, aqueous work-up, extraction with organic solvents, distillation, crystallization, column chromatography, and high pressure liquid chromatography (HPLC) on normal phase or reversed phase. The isolated yield of the indole or the indolenine is at least 15%, preferably at least 30%, preferably at least 50%, preferably at least 60%, preferably at least 70%, preferably at least 80%, preferably at least 90%. The isolated yield is calculated as (mole of the isolated indole or indolenine/mole of the aryl hydrazine)×100%.

Preferably, the ionic liquid of the present disclosure tolerates a variety of functional groups on the aryl hydrazine and/or the alkyl ketone or the alkyl aldehyde. An exemplary aryl hydrazine may have the following structure (VI)

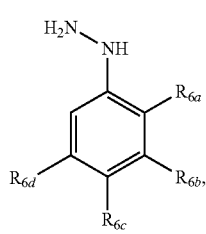

(VI)

or a salt thereof, a solvate thereof, a stereoisomer thereof, or a mixture thereof, where $R_{6a}$, $R_{6b}$, $R_{6c}$, and $R_{6d}$ are each independently selected from the group consisting of a hydrogen, an optionally substituted alkyl, an optionally substituted cycloalkyl, an optionally substituted arylalkyl, an optionally substituted aryl, an optionally substituted alkoxy, an optionally substituted alkanoyl, an optionally substituted aroyl, a hydroxyl, a halogen, a nitro, and a cyano. Examples of suitable aryl hydrazine include, without limitation, phenyl hydrazine, 1-naphthalenyl hydrazine, 4-methylphenylhydrazine, 4-dodecylphenylhydrazine, 2,5-dimethylphenylhydrazine, 3,4-dimethylphenylhydrazine, 4-isopropylphenylhydrazine, 4-methoxyphenylhydrazine, 4-hydroxyphenylhydrazine, 2-chlorophenylhydrazine, 4-chlorophenylhydrazine, 5-chloro-2-methylphenylhyirazine, 2,4-dichlorophenylhydrazine, 2-bromophenylhydrazine, 3-bromophenylhydrazine, 4-bromophenylhydrazine, 4-fluorophenylhydrazine, 4-iodophenylhydrazine, 4-cyanophenylhydrazine, 3-nitrophenylhydrazine, and 4-(trifluoromethyl)phenylhydrazine. In a preferred embodiment, $R_{6a}$, $R_{6b}$, $R_{6c}$, and $R_{6d}$ are independently a hydrogen, an electron-donating functional group including an optionally substituted alkyl, an optionally substituted cycloalkyl, an optionally substituted arylalkyl, an optionally substituted aryl, an optionally substituted alkoxy, a hydroxyl, or a weak electron-withdrawing functional group such as a halogen.

An exemplary alkyl ketone may have the following structure (VII)

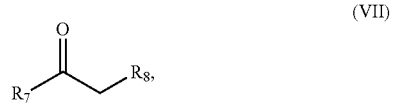

(VII)

or a salt thereof, a solvate thereof, a stereoisomer thereof, a tautomer thereof, or a mixture thereof, where $R_7$ is selected from the group consisting of an optionally substituted alkyl, an optionally substituted cycloalkyl, an optionally substituted arylalkyl, an optionally substituted aryl, and an optionally substituted heterocyclyl and $R_8$ is selected from the group consisting of hydrogen, an optionally substituted alkyl, an optionally substituted cycloalkyl, an optionally substituted arylalkyl, an optionally substituted aryl, and an optionally substituted heterocyclyl. In one or more embodiments, the $R_7$ and $R_8$ groups may together form a cyclic ring, and the alkyl ketone of structure (VII) may be cyclohexanone, 2-methylcyclohexanone or 5,5-dimethyl-1,3-cyclohexanedione. Other non-limiting examples of suitable alkyl ketones include acetone, methyl ethyl ketone, methyl isopropyl ketone, methyl isobutyl ketone, phenylacetone, ethyl pyruvate, 2-nonanone, 5-nonanone, 3-pentanone, and 2-dodecanone.

An exemplary alkyl aldehyde may have the following structure (VIII)

(VIII)

or a salt thereof, a solvate thereof, a stereoisomer thereof, a tautomer thereof, or a mixture thereof, where $R_9$ is selected from the group consisting of hydrogen, an optionally substituted alkyl, an optionally substituted cycloalkyl, an optionally substituted arylalkyl, an optionally substituted aryl, and an optionally substituted heterocyclyl. Examples of suitable alkyl aldehyde include, without limitation, acetaldehyde, propionaldehyde, butyraldehyde, 4-pentenal, valeraldehyde, 3-methylbutyraldehyde, 3,3-dimethylbutyraldehyde, hexanal, 3-methylhexanal, heptaldehyde, octanal, 3-cyclohexylpropionaldehyde, nonanal, 3,5,5-trimethylhexanal, citronellal, 7-hydroxycitronellal, dodecyl aldehyde, 3-(3-chlorophenyl)propionaldehyde, hydrocinnamaldehyde, 3-phenylbutyraldehyde, 3-(4-methoxyphenyl)propionaldehyde, and 3-benzyloxypropionaldehyde.

The ionic liquid of the present disclosure in any of its embodiments is capable to be used as a catalyst for the aforementioned method of synthesizing indole or indolenine. In a preferred embodiment, the ionic liquid is

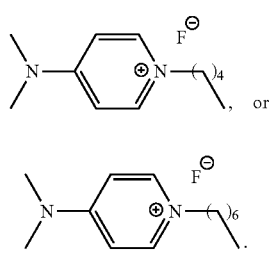

In a preferred embodiment, the formed indole and indolenine by the method described herein is at least one selected from the group consisting of

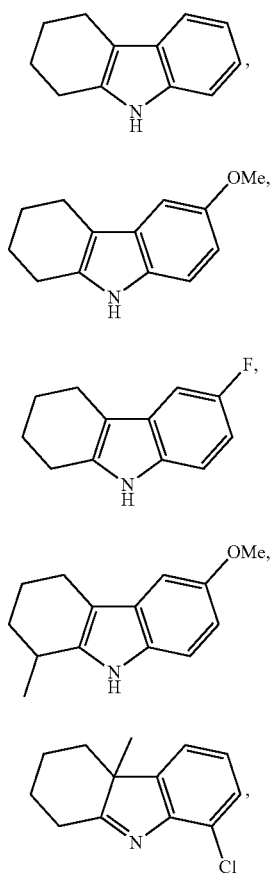

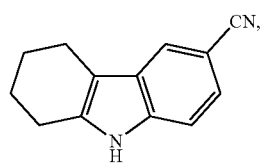

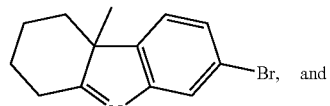

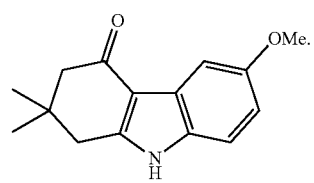

Tetrazole is a nitrogen rich five membered ring which serves as an isosteric substituent of carboxylic acid. It serves as an important structural component in molecules of pharmaceutical interest [M. Malik, M. Wani, S. Al-Thabaiti, R. Shiekh, J. Incl. Phenom. Macrocycl. Chem., 78 (2014) 15-37, incorporated herein by reference in its entirety]. The presence of 1H-tetrazole species has been known to favorably enhance metabolic resistance and pharmacokinetic properties in drug molecules [L. V. Myznikov, A. Hrabalek, G. I. Koldobskii, Chem. Heterocycl. Compd., 43 (2007) 1-9, incorporated herein by reference in its entirety]. Tetrazoles are also important ligands in coordination chemistry, and crucial intermediates in synthetic transformations [S. J. Wittenberger, Org. Prep. Proced. Int., 26 (1994) 499-531; R. N. Butler, Tetrazoles, in: A. R. Katritzky, C. W. Rees, E. F. V. Scriven (Eds.) Comprehensive heterocyclic chemistry II, Pergamon, Oxford, 1996, pp. 621-678; and P. N. Gaponik, S. V. Voitekhovich, O. A. Ivashkevich, Russ. Chem. Rev., 75 (2006) 507, each incorporated herein by reference in their entirety]. As an structural analog and metabolically stable substitute of a carboxyl group, the tetrazole ring is extensively studied in molecular design and synthesis of modified amino acids and peptidomimetics [S. J. Wittenberger, Org. Prep. Proced. Int., 26 (1994) 499-531; and R. J. Herr, Bioorg. Med. Chem., 10 (2002) 3379-3393, each incorporated herein by reference in their entirety]. Synthesis and application of tetrazoles has become increasingly valued and made significant scientific impact in the last two decades [A. Sarvary, A. Maleki, Molec. Divers., 19 (2015) 189-212; and A. Maleki, A. Sarvary, RSC Adv., 5 (2015) 60938-60955, each incorporated herein by reference in their entirety].

The term click chemistry was introduced by Sharpless et al. by preforming a [2+3]cycloaddition between a nitrile and an azide moiety to form the tetrazole [Z. P. Demko, K. B. Sharpless, Angew. Chem. Int. Ed., 41 (2002) 2110-2113, incorporated herein by reference in its entirety]. Tetrazole formation through click chemistry is often catalyzed by zinc metals [Z. P. Demko, K. B. Sharpless, J. Org. Chem., 66 (2001) 7945-7950; S. Vorona, T. Artamonova, Y. Zevatskii, L. Myznikov, Synthesis, 46 (2014) 781-786; and S. Hajra, D. Sinha, M. Bhowmick, J. Org. Chem., 72 (2007) 1852-1855, each incorporated herein by reference in their entirety]. Fluoride ions have a strong affinity for silicon resulting in the release of active azide species from silicon-protected azide starting materials. In some previous methods, neat TBAF or 1,8-diazabicycloundec-7-ene (DBU)-based ionic liquids with fluoride counter anions have been used in click reactions for tetrazole synthesis. For instance, Amantini et al. recently developed metal free conditions for click reaction by using tetrabutyl ammonium fluoride (TABF) as a catalyst for tetrazole formation though nitrile species and trimethylsilyl azide [D. Amantini, R. Beleggia, F. Fringuelli, F. Pizzo, L. Vaccaro, J. Org. Chem., 69 (2004) 2896-2898, incorporated herein by reference in its entirety].

According to a fourth aspect, the present disclosure relates to a method of synthesizing a tetrazole. The method involves reacting a nitrile with an azide in the presence of the ionic liquid of the first aspect, thereby forming the tetrazole.

In one or more embodiments, the ionic liquid is present in an amount of 5 mol % to 60 mol %, preferably 10 mol % to 50 mol %, preferably 15 mol % to 45 mol %, preferably 20 mol % to 40 mol %, preferably 25 mol % to 35 mol %, or about 30 mol % relative to moles of the nitrile. Although an ionic liquid concentration higher than 60 mol % (e.g. up to 70 mol %, 80 mol %, 90 mol %, 100 mol % relative to moles of the aryl hydrazine) may be used and the method will still proceed as intended. In a preferred embodiment, reacting the nitrile with the azide in the presence of the ionic liquid is conducted in neat (solvent-free) condition. It is equally envisaged that the reaction may be adapted to be performed in a solvent such as dimethylformamide, tetrahydrofuran, ethyl acetate, acetonitrile, dimethyl sulfoxide, methylene chloride, chloroform, nitrobenzene, methanol, ethanol, n-propanol, isopropyl alcohol, and mixtures thereof. In a preferred embodiment, a molar ratio of the nitrile to the azide is in a range of 1:2 to 1:6, preferably 2:5 to 1:4, or about 1:3.

In a preferred embodiment, the aforementioned reaction is performed under agitation at a temperature of up to 180° C., preferably 30-150° C., preferably 50-140° C., preferably 70-120° C., preferably 80-110° C. and has a reaction time of up to 72 hours, preferably 1-48 hours, preferably 4-36 hours, preferably 8-24 hours, preferably 12-18 hours. An external heat source, such as a water bath or an oil bath, an oven, microwave, or a heating mantle, may be employed to heat the reaction mixture. The reaction mixture may be agitated throughout the duration of the reaction by employing a rotary shaker, a magnetic stirrer, or an overhead stirrer. In another embodiment, the reaction mixture is left to stand (i.e. not agitated). In one embodiment, the reaction mixture is stirred by a magnetic stirrer at a speed of at least 300 rpm, preferably at least 500 rpm, preferably at least 700 rpm, preferably at least 900 rpm. In one embodiment, the reaction mixture is sonicated in an ultrasonic bath or with an ultrasonic probe.

The progress of the aforementioned reaction may be monitored by aforementioned methods known to those skilled in the art. Preferably, thin layer chromatography is used. The tetrazoles formed by the method disclosed herein are isolated and purified by employing aforementioned methods known to those skilled in the art. The isolated yield of the tetrazole is at least 40%, preferably at least 50%, preferably at least 60%, preferably at least 70%, preferably at least 80%, preferably at least 90%. The isolated yield is calculated as (mole of isolated tetrazole/mole of the nitrile)×100%.

Preferably, the ionic liquid of the present disclosure tolerates a variety of functional groups on the nitrile and/or the azide. An exemplary nitrile may have the following structure (IX)

$$R_{10}\text{—}C\text{≡}N \qquad (IX),$$

or a salt thereof, a solvate thereof, a stereoisomer thereof, or a mixture thereof, where $R_{10}$ is selected from the group consisting of an optionally substituted alkyl, an optionally substituted cycloalkyl, an optionally substituted arylalkyl, an optionally substituted aryl, and an optionally substituted heterocyclyl. Preferably, $R_{10}$ is an optionally substituted aryl. Examples of suitable nitriles include, without limitation, benzonitrile, p-tolunitrile, 4-methoxybenzonitrile, 4-(dimethylamino)benzonitrile, 4-(diethylamino)benzonitrile, 4-fluorobenzonitrile, 4-chlorobenzonitrile, 4-bromobenzonitrile, 3-(trifluoromethyl)benzonitrile, 4-(trifluoromethyl)benzonitrile, 2-fluoro-4-(trifluoromethyl)benzonitrile, 2-chloro-6-fluorobenzonitrile, 3-chloro-4-fluorobenzonitrile, 4-fluoro-3-nitrobenzonitrile, 2-nitro-4-(trifluoromethyl)benzonitrile, 4-amino-2-(trifluoromethyl)benzonitrile, 4-(trifluoromethoxy)benzonitrile, 4-(1H-pyrrol-1-yl)benzonitrile, 3-(hydroxymethyl)benzonitrile, 3-(bromomethyl)benzonitrile, 4-(hydroxymethyl)benzonitrile, 3-(2-oxiranylmethoxy)benzonitrile, 3-(acetoxymethyl)benzonitrile, 4-(2-oxiranylmethoxy)benzonitrile, 4-(acetoxymethyl)benzonitrile, 4-(2-hydroxyethyl)benzonitrile, 4-(methylamino)benzonitrile, and 3-(methylamino)benzonitrile. Exemplary azides include, without limitation, a silyl-protected azide, such as trimethylsilyl azide and triethylsilyl azide, sodium azide, potassium azide, lithium azide, tetrabutylammonium azide, benzyl azide, p-toluenesulfonyl azide, 2,4,6-triisopropylbenzenesulfonyl azide, alkyl azides, dialkyl aluminum azides, 1-butyl-3-methylimidazolium azide, diphenyl phosphorazidate, tetramethylguanidinium azide, tributyltin azide, and substituted phenyl azide. In preferred embodiments, the azide is a silyl-protected azide. Exemplary silyl-protecting groups include, without limitation, trimethylsilyl, triethylsilyl, triisopropylsilyl, tributylsilyl, tert-butyldimethylsilyl, tert-butyldiphenylsilyl, and dimethylthexylsilyl. Most preferably, the azide is trimethylsilyl azide.

The ionic liquid of the present disclosure in any of its embodiments can be used as a catalyst for the aforementioned method of synthesizing tetrazole. In a preferred embodiment, the ionic liquid is

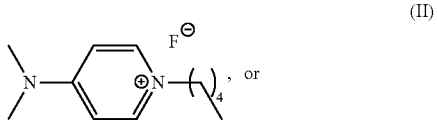

(II)

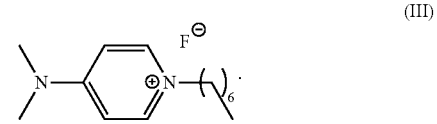

(III)

In a preferred embodiment, the formed tetrazole by the method described herein is at least one selected from the group consisting of

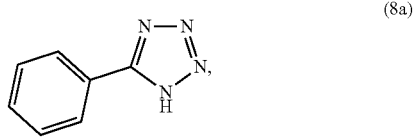

(8a)

-continued

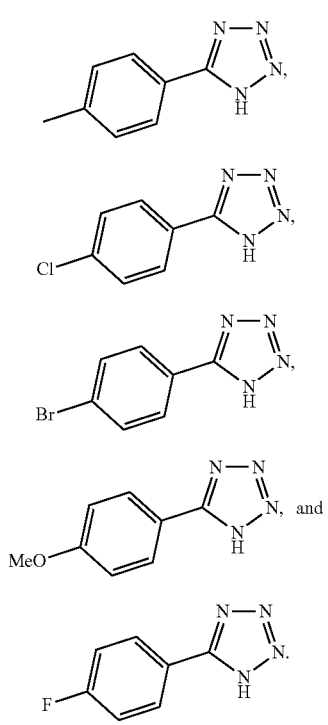

Having generally described this disclosure, a further understanding can be obtained by reference to certain specific examples such as protocols for preparing and characterizing the ionic liquid, and methodologies of using the ionic liquid in synthesizing indoles/indolenines and tetrazoles. The examples below are provided herein for purposes of illustration only and are not intended to limit the scope of the claims.

Example 1

Material and Methods

N,N-dimethylpyridin-4-amine (DMAP) (≥99.0%), pentyl bromide, heptyl bromide, toluene (≥99.5%), potassium fluoride (≥99.0%) were purchased from Sigma Aldrich and used without further purification unless otherwise stated. Thin layer chromatography (TLC) was carried out using silica gel 60 aluminum-backed plates 0.063-0.200 mm. Analytical grade solvents such as ethyl acetate (EtOAc), diethyl ether, hexane and methanol etc. were used. Short wavelength UV radiation at 254 nm was used for visualization of TLC plates. Staining mixture such as basic potassium permanganate or vanillin was also used for visualization of TLC plates. Infrared (IR) spectra were recorded on Bruker Vector-22 spectrometer. The $^1$H NMR spectra were recorded on Bruker spectrometers at 300 MHz, 400 MHz, 500 MHz, and 600 MHz, while $^{13}$C NMR spectra were recorded at 75 MHz, 100 MHz, 125 MHz, 150 MHz in deuterated solvents. The chemical shifts were recorded on the δ-scale (ppm) using residual solvents as an internal standard (DMSO; $^1$H 2.50, $^{13}$C 39.43 and CHCl$_3$; $^1$H 7.26, $^{13}$C 77.16). Coupling constants were calculated in Hertz (Hz) and multiplicities were labelled s (singlet), d (doublet), t (triplet), q (quartet), quint (quintet) and the prefixes br (broad) or app (apparent) were used. Mass spectra (EI$^+$ and FAB) were recorded on Finnigan MAT-321 IA, Germany. Melting points of solids were determined using a Stuart™ melting point SMP3 apparatus.

Example 2

In the present study, new DMAP-based ionic liquids have been synthesized via N-alkylation, and successfully employed as catalysts for Fischer indole/indolenine and 1H-tetrazole formation. The commercially available DMAP was treated with alkyl bromide to get the corresponding N-alkylated cations with bromide anions. Owing to the documented nature of fluoride ions as catalyst and as a mild base in various organic reactions [J. H. Clark, Chem. Rev., 80 (1980) 429-452, incorporated herein by reference in its entirety], the aforementioned N-alkylated cations with bromide ions were subjected to anion exchange with fluoride ions. The resulting DMAP-IL (dimethylamino pyridinium with fluoride counter anion) could effectively serve as a substitute for tetra butyl ammonium fluoride (TBAF), a well-known catalyst and IL that has been used to promote different chemical reactions (FIG. 2) [J. H. Clark, Chem. Rev., 80 (1980) 429-452; A. Hameed, R. D. Alharthy, J. Iqbal, P. Langer, Tetrahedron, 72 (2016) 2763-2812; and D. Amantini, R. Beleggia, F. Fringuelli, F. Pizzo, L. Vaccaro, J. Org. Chem., 69 (2004) 2896-2898, each incorporated herein by reference in their entirety]. The DMAP-based ionic liquids (2, 3) [or (II) and (III)] with fluoride counter anions were then investigated for their efficiency as catalysts for synthesis of tetrahydro-1H-carbazole (indoles)/methyl tetrahydro-1H-carbazole (indolenines) (FIG. 3B) and 1H-tetrazole (FIG. 4B) compounds. (FIG. 1).

Figure 2:
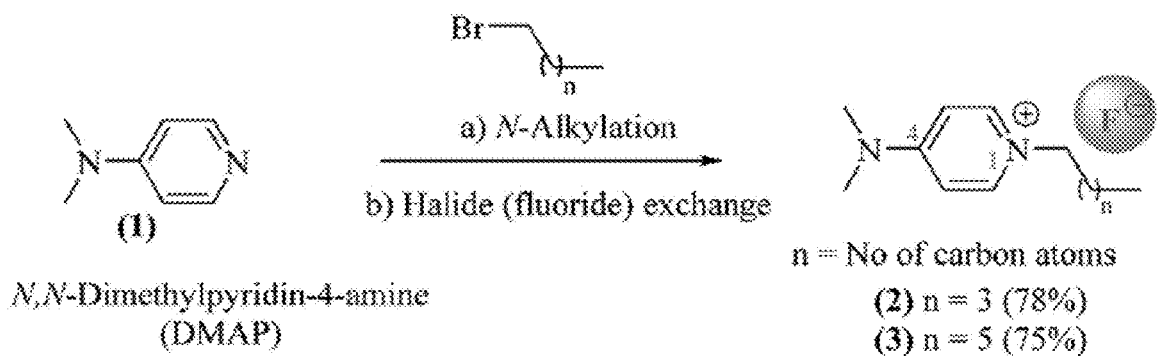
FIG. 2 is a reaction scheme for the synthesis of ionic liquids (II) and (III).

A general scheme for the preparation of DMAP-based ionic liquids (DMAP-ILs) comprises two steps i.e. a) N-alkylation of dimethylamino pyridine (DMAP), and b) exchange of bromide counter anion with fluoride anion. The yields of final DMAP-ILs (2, 3) [or (II) and (III)] with fluoride counter anion were found to be 78% and 75%, respectively (FIG. 2). The newly synthesized DMAP-ILs were then employed as catalyst in organic synthesis; 1) Fischer indole synthesis and 2) 1H-tetrazole formation. The catalyst (2, 3) can be easily removed via simple aqueous work-up from the reaction mixture.

Figure 4A:
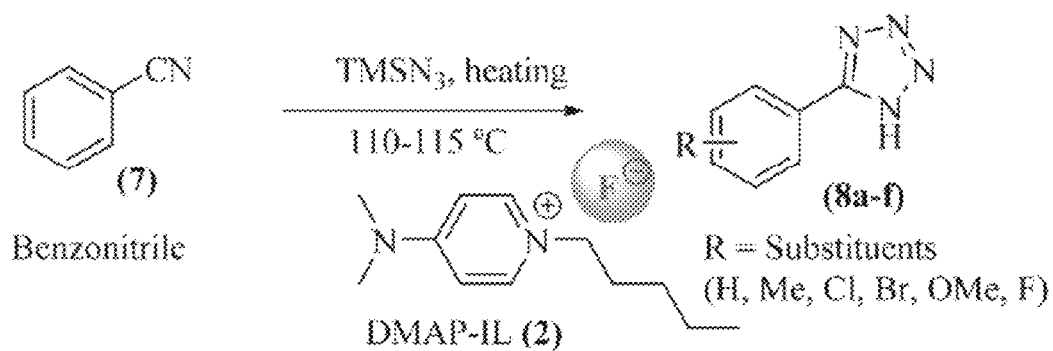
FIG. 4A shows an exemplary tetrazole synthesis catalyzed by the ionic liquid.

The DMAP-based ionic liquids were successfully employed as catalysts with minimum loading (0.2 equivalent) for tetrazole formation. Moreover, the removal of DMAP-based ionic liquids from the reaction mixture was also found easy. The catalytic efficiency of DMAP-IL (2) [or (II)] in click chemistry of 1H-tetrazole formation was explored by reacting different benzonitriles with an azide source, i.e. trimethylsilyl azide, under solvent-free conditions (FIG. 4A).

Figure 3A:
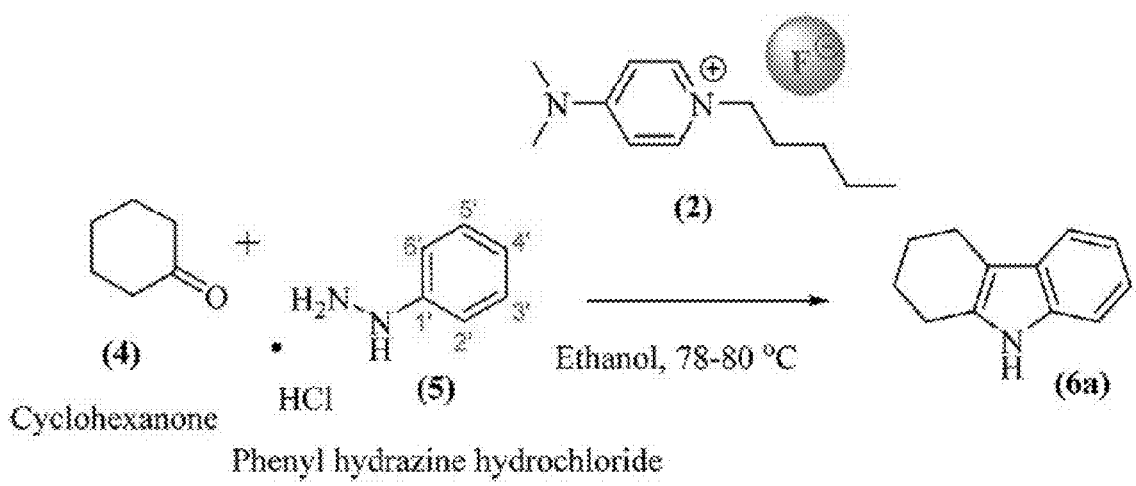
FIG. 3A shows an exemplary Fischer indole synthesis catalyzed by the ionic liquid.

A typical reaction of Fischer indole synthesis, between phenyl hydrazine and cyclohexanone, was carried out by using DMAP-based ionic liquids as catalyst, in ethanol as a solvent, affording the desired product 7 in excellent yield. The reaction conditions were examined by varying the amount of DMAP-IL catalysts (2, 3) [or (II) and (III)] as shown in Table 1. The percentage yield (89%) of corresponding indole (2,3,4,9-tetrahydro-1H-carbazole) up on addition of 0.2 equiv. of DMAP based IL (2) [or (II)], was found to be comparable to the yield (91%) obtained while using 0.3 equiv. of DMAP-IL. Accordingly, DMAP-based ionic liquid (2) [or (II)] as catalyst with 0.2 equiv. was opted for further investigation on the scope of DMAP-based catalyst (FIG. 3A).

TABLE 1

Studies of Fischer indole synthesis using DMAP-ILs

| Entry | DMAP-ILs | Equivalent[a] | % yield (6a) |
|---|---|---|---|
| 1 | 2 | 0.05 | 68 |
| 2 | 2 | 0.2 | 89 |
| 3 | 2 | 0.3 | 91 |
| 4 | 3 | 0.05 | 48 |
| 5 | 3 | 0.2 | 64 |

[a]Catalytic amount of DMAP-ILs in ethanol.

Figure 3B:
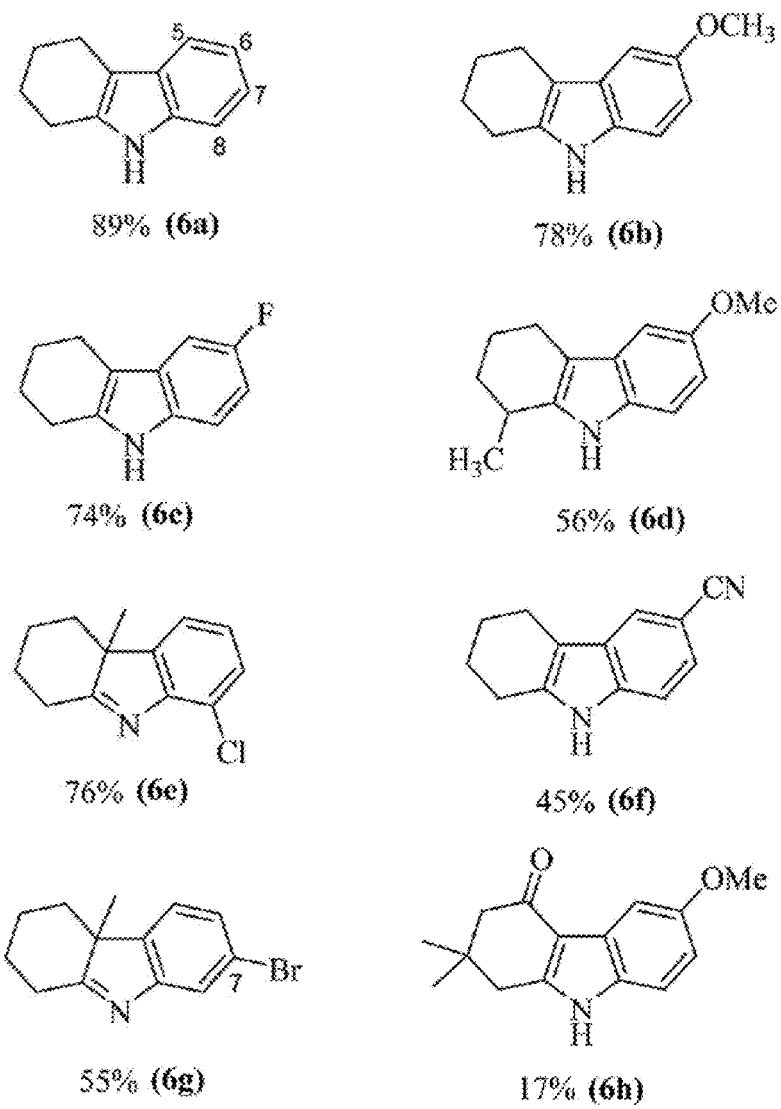
FIG. 3B shows a library of indole and indolenine compounds synthesized by using the ionic liquid (II).

By utilizing the most advantageous conditions, a range of different substituted phenyl hydrazine hydrochlorides were treated with cyclohexanone or 2-methyl cyclohexanone to furnish the corresponding tetrahydro-1H-carbazole (indoles)/methyl tetrahydro-1H-carbazole (indolenines) derivatives (6a-h) in variable yields (FIG. 3B). No indole formation was observed in case of 2,4-dinitrophenyl hydrazine even on increasing the temperature (up to 100° C.) and reaction time to 14 h. It may be due to the electron withdrawing effects of nitro groups which hampered the requisite cyclization of phenyl ring with cyclohexane to complete the corresponding indole scaffold. However, the reaction occurred smoothly with phenyl hydrazine, 4'-methoxy and 4'-fluorophenyl hydrazine to afford indoles 6a (89%), 6b (78%) and 6c (75%) in good yields. The slight low yield (75%) of 6'-fluoro substituted indole 6c may be due to electron withdrawing effect of flouro substituent. The reaction of 2-methyl cyclohexanone with methoxyphenyl hydrazine in the presence of catalyst (2) yielded corresponding indole (6d) in modest yields (56%). While the reaction of 2-methyl cyclohexanone with 2'-chloro substituted phenyl hydrazine gave corresponding 8'-chloro indolenine (6e) in 76% and with 3'-bromo substituted phenyl hydrazine afforded 7'-bromo indolenine (6g) as a major regioisomeric product in 55% yield. The reaction of 4'-cyano substituted phenyl hydrazine with cyclohexanone produce corresponding indole (6f) in moderate yield (60%) due to strong electron withdrawing effect of cyano group. The reaction of 1,3-cyclohexanediones (dimedone) with phenylhydrazine, gave low yield (17%) of corresponding indole (6h) due to the formation of stable N-phenylhydrazone intermediate which is difficult to activate for the next [3,3] sigmatropic rearrangement to furnish the corresponding indole (6h) (FIG. 3B).

Further, the click reaction of 1H-tetrazole formation between benzonitrile and trimethylsilyl azide (TMSN$_3$) was carried out in the presence of DMAP-IL (0.3 equiv.) as a catalyst. The reaction occurred smoothly and gave the desired 1H-tetrazole in good to moderate yield (78-48%). TMSN$_3$ was used as an azide source. Because of fluoride anion's greater affinity for silyl group, there is a much more efficient release of active azide for click reaction of tetrazole formation [D. Amantini, R. Beleggia, F. Fringuelli, F. Pizzo, L. Vaccaro, J. Org. Chem., 69 (2004) 2896-2898; and P. G. M. Wuts, T. W. Greene, Greene's Protective Groups in Organic Synthesis, Wiley, 2006, each incorporated herein by reference in their entirety]. To further broaden the scope of DMAP-based ionic fluoride liquid (2) [or (II)] as a catalyst, click reactions with different substituted benzonitriles and TMSN$_3$ were carried out. In all cases, the 1H-phenyl tetrazoles (8a-f) were obtained in good yields. The yield of unsubstituted phenyl tetrazole (8a, 48%) was found low in comparison to methyl substituted phenyl tetrazole (8b, 78%). This could be due to electron donating effect of methyl group which enhanced the reactivity of cyano group.

Figure 4B:
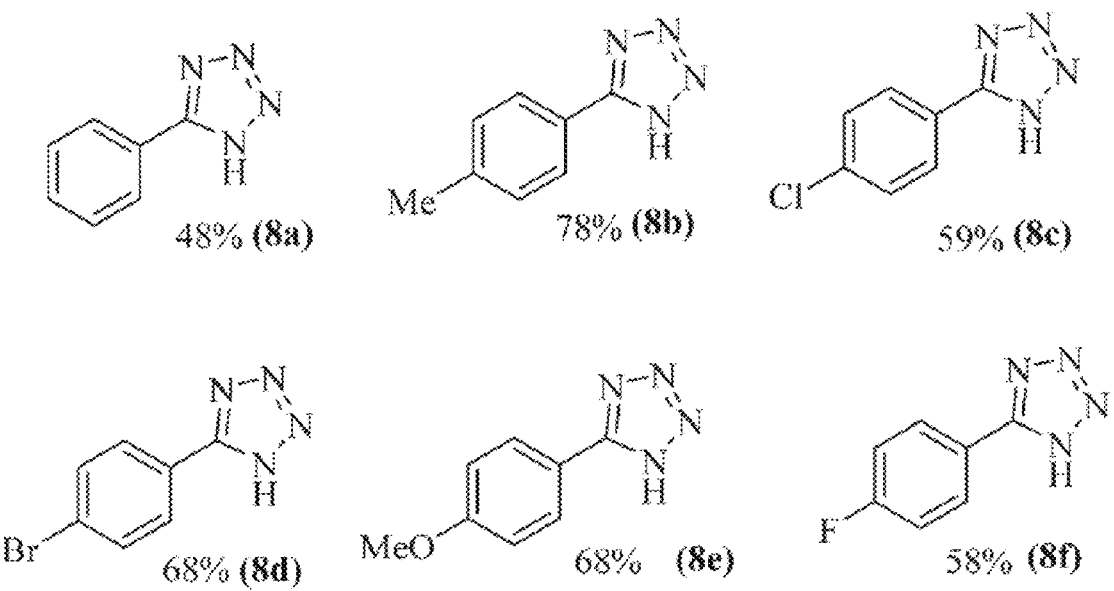
FIG. 4B shows a library of tetrazole compounds synthesized by using the ionic liquid (II).

The yields of halogen substituted (Cl, Br, F) phenyl tetrazoles (8c, 59%), (8d, 68%), and (8f, 58%) were found less compared to (8b). This is due to electron withdrawing effect of halogen substituents. Further among halogen substituted phenyl tetrazoles, the percentage yield with more electronegative substituents F and Cl was found to be less as compared to least electronegative substituents Br. The yield of methoxy substituent bearing phenyl tetrazole (8e) was also found to be good (70%). The structures of synthesized compounds 8a-f were confirmed with NMR spectroscopy and mass spectrometry (FIG. 4B).

Example 3

General synthetic procedure for DMAP-based ionic fluoride salts 2 and 3 [or (II) and (III)]

An oven dried round bottomed flask was cooled to room temperature and charged with N,N-dimethylpyridin-4-amine (500 mg, 4.09 mmol, 1 equiv.), toluene (5 mL), and corresponding alkyl bromide (1 equiv.) at room temperature. The reaction mixture was heated at reflux (118-120° C.) for 2 to 12 h until no starting material was observed on TLC analysis. On cooling the resulting ionic salts, as oily solid which after some time became thick oil, was separated and washed further with cooled toluene and dried in vacuo. The obtained crude ionic liquids were treated with aqueous solution of silver fluoride (4-5 mL, 1 equiv.). Afterward, the precipitates of silver bromide were removed by filtration and then water was evaporated with freeze drying process. The resulting residue was dissolved in chloroform, filtered and evaporated on rotary evaporator. The obtained materials were occasionally washed with cooled toluene or hexane to get the final desired products DMAP-ILs (2 and 3) [or (II) and (III)]. The obtained DMAP-ILs 2 and 3 were fully characterized with $^1$H, $^{13}$C-NMR, IR, UV spectroscopy and mass spectrometry.

Example 4

Spectral Data of DMAP-Based Ionic Fluoride Salt 2 [4-(Dimethylamino)-1-pentylpyridin-1-ium Fluoride], or (II)

Light yellow oil, (165 mg, 78%). $^1$H NMR (400 MHz, DMSO-d$_6$): $\delta_H$ 8.28 (2H, d, J=7.6 Hz, ArH), 7.02 (2H, d, J=7.6 Hz, ArH), 4.14 (2H, t, J=7.2 Hz, CH$_2$), 3.17 (6H, s, C(CH$_3$)$_2$), 1.75 (2H, quint, J=7.4 Hz, CH$_2$), 1.28 (2H, app quint, J=7.4 Hz, CH$_2$), 1.18 (2H, app quint, J=7.4 Hz, CH$_2$), 0.85 (3H, t, 7.2 Hz, CH$_3$) ppm; $^{13}$C NMR (100 MHz, DMSO-d$_6$): $\delta_C$ 155.8 I, 141.9 (CH×2), 107.6 (CH×2), 56.6 (CH$_2$), 39.7 (CH$_3$×2), 29.9 (CH$_2$), 27.5 (CH$_2$), 21.5 (CH$_2$), 13.8 (CH$_3$) ppm. F$^{19}$ NMR (400 MHz, CD$_3$CN): $\delta_F$ −127.4 ppm. MS-EI m/z, 193.2 (M$^+$-F$^−$). EI-HRMS (M$^+$-F$^−$) C$_{12}$H$_{21}$N$_2$ Found 193.1722, Calculated 193.1705.

Example 5

Spectral Data of DMAP-Based Ionic Fluoride Salt 3 [4-(Dimethylamino)-1-heptylpyridin-1-ium Fluoride], or (III)

Yellow oil, (180 mg, 75%), IR ($v_{max}$, cm$^{−1}$): (Liquid, CHCl$_3$) 3442, 2929, 1650, 1569, 1403, 1175, 833. $^1$H NMR (400 MHz, DMSO-d$_6$): $\delta_H$ 8.31 (2H, d, J=8.0 Hz, ArH), 7.02 (2H, d, J=7.6 Hz, ArH), 4.15 (2H, t, J=7.0 Hz, CH$_2$), 3.17 (6H, s, C(CH$_3$)$_2$), 1.75 (2H, quint, J=7.4 Hz, CH$_2$), 1.27-1.19 (8H, m, (CH$_2$)$_4$), 0.85 (3H, t, J=6.6 Hz, CH$_3$) ppm; $^{13}$C NMR (100 MHz, DMSO-d$_6$): $\delta_C$ 155.8 I, 142.1 (CH×2), 107.7 (CH×2), 56.6 (CH$_2$), 39.7 (CH$_3$×2), 31.1 (CH$_2$), 30.3

(CH$_2$), 28.1 (CH$_2$), 25.3 (CH$_2$), 21.9 (CH$_2$), 13.8 (CH$_3$) ppm. F$^{19}$ NMR (400 MHz, CD$_3$CN): $\delta_F$ −127.5 ppm. MS-ESI m/z (%), 221.1 (M$^+$-F$^-$), 220, 219; EI-HRMS (M$^+$-F$^-$) C$_{14}$H$_{25}$N$_2$ Found 221.1999, Calculated 221.2018.

Example 6

Thermal Studies

Figure 5A:
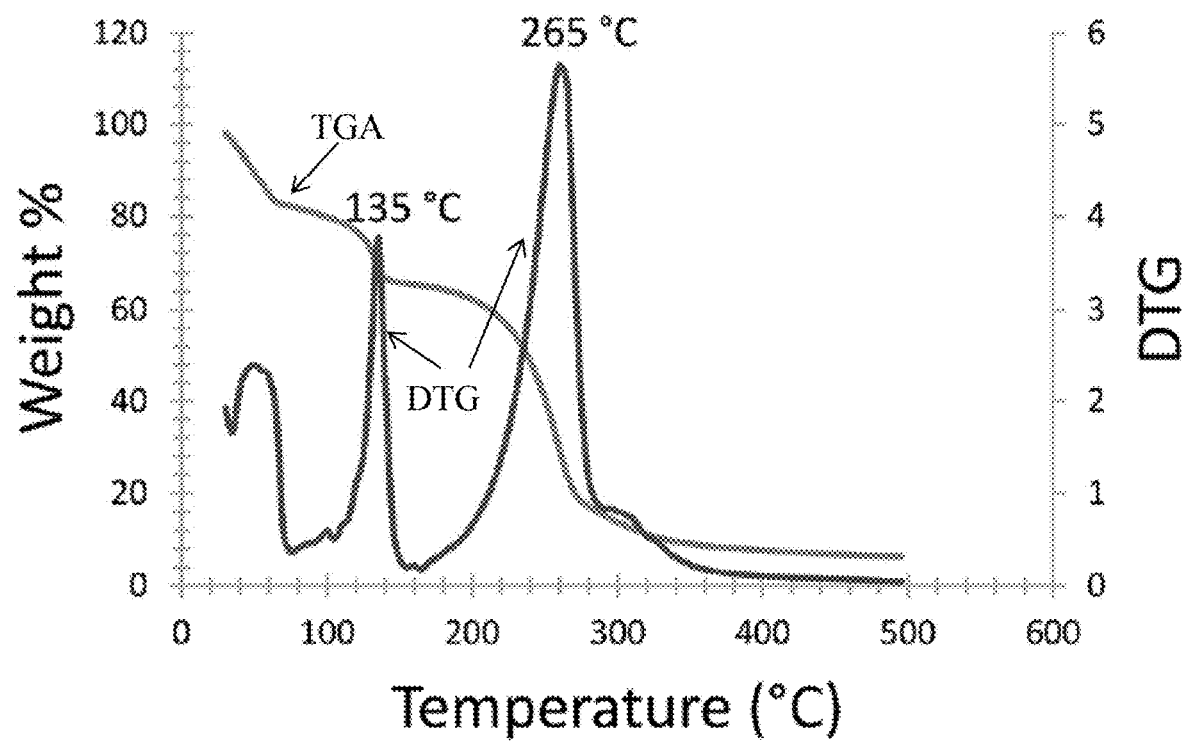
FIG. 5A is an overlay of thermogravimetric analysis (TGA) and derivative thermogravimetry (DTG) of the ionic liquid (II).
Figure 5B:
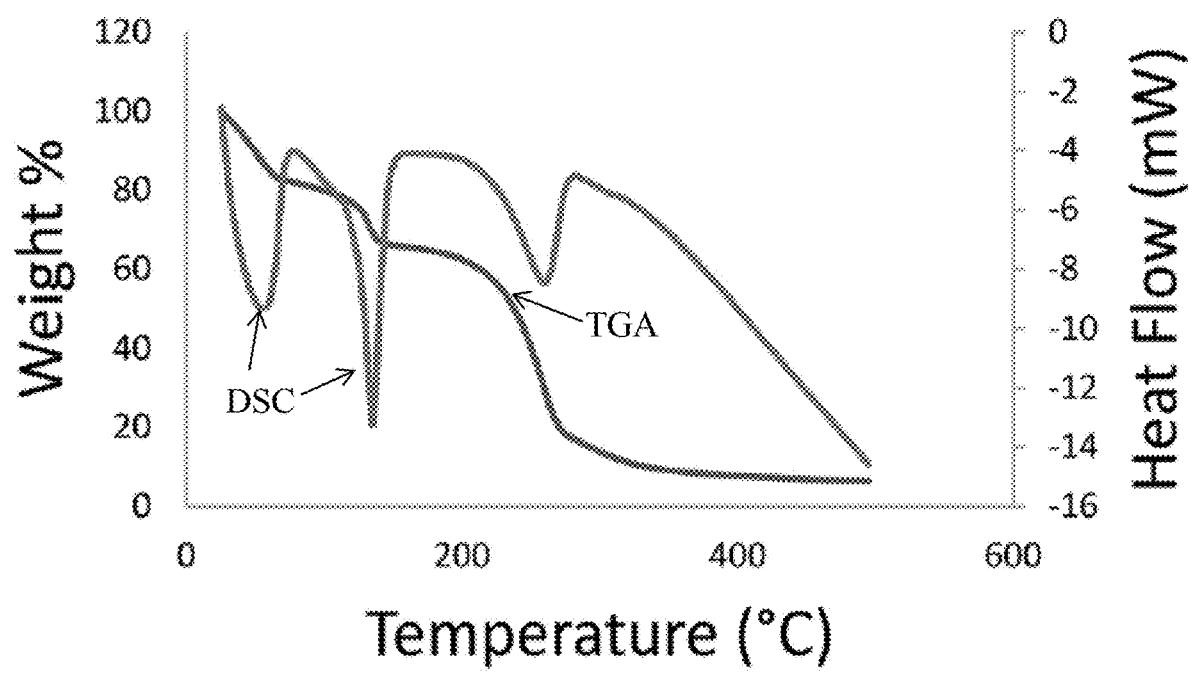
FIG. 5B is an overlay of TGA and differential scanning calorimetry (DSC) of the ionic liquid (II).

Thermal studies of DMAP-Ils (2, 3) [or (II) and (III)] were also conducted to signify the efficiency of catalyst in temperature dependent reactions. Thermal stability and decomposition pattern was evaluated by carrying out thermogravimetric analysis (TGA), derivative thermogravimetry (DTG), and differential scanning calorimetry (DSC) (FIGS. 5A-D). FIG. 5A shows overlap of thermogravimetric (TGA) graph and its first derivative (DTG) for compound (2) [or (II)], and FIG. 5B shows overlap of TGA and DSC graphs. In the first step, there is a gradual loss of weight (16%), in the temperature range from ambient to 70° C., which is probably due to the loss of water molecules. Immediately after this step, the onset of degradation is observed in the temperature range 70° C. to 140° C. where weight loss of 16% is observed, from DTG the first decomposition temperature appears at 135° C. In the third and final step remaining weight loss (60%) is observed in the range 140° C. to 310° C., the decomposition temperature for this step is observed at 265° C.

Figure 5C:
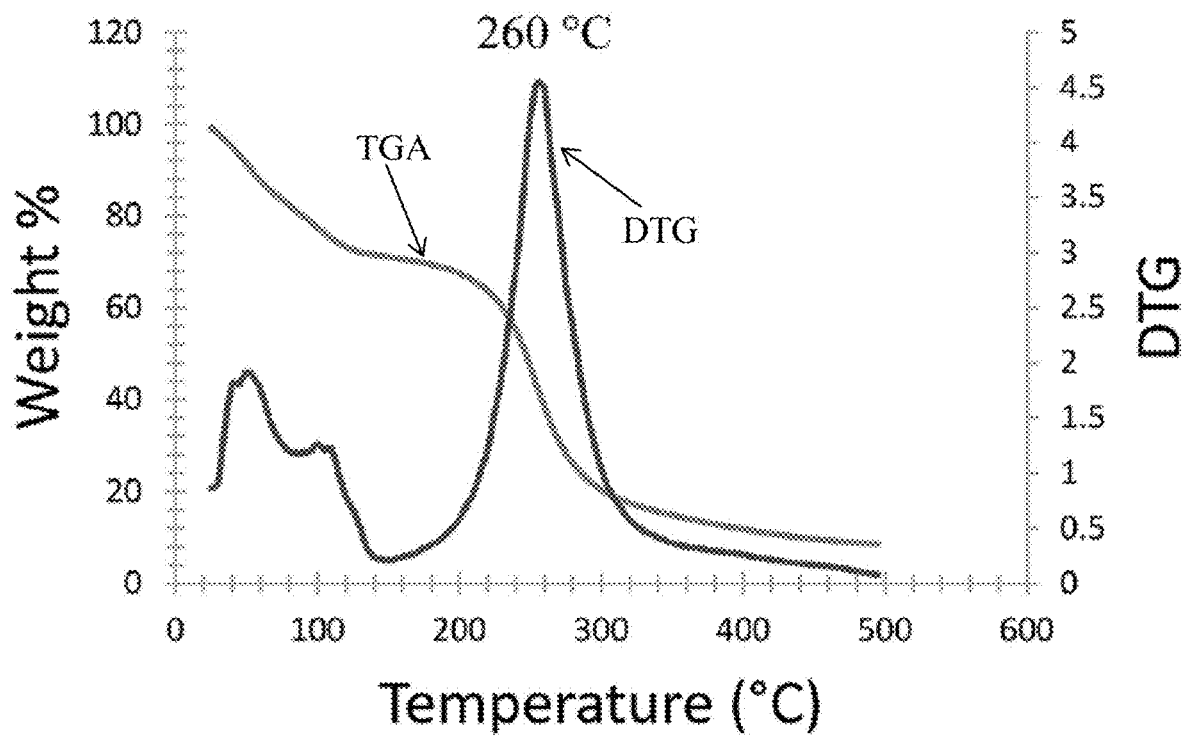
FIG. 5C is an overlay of TGA and DTG of the ionic liquid (III).
Figure 5D:
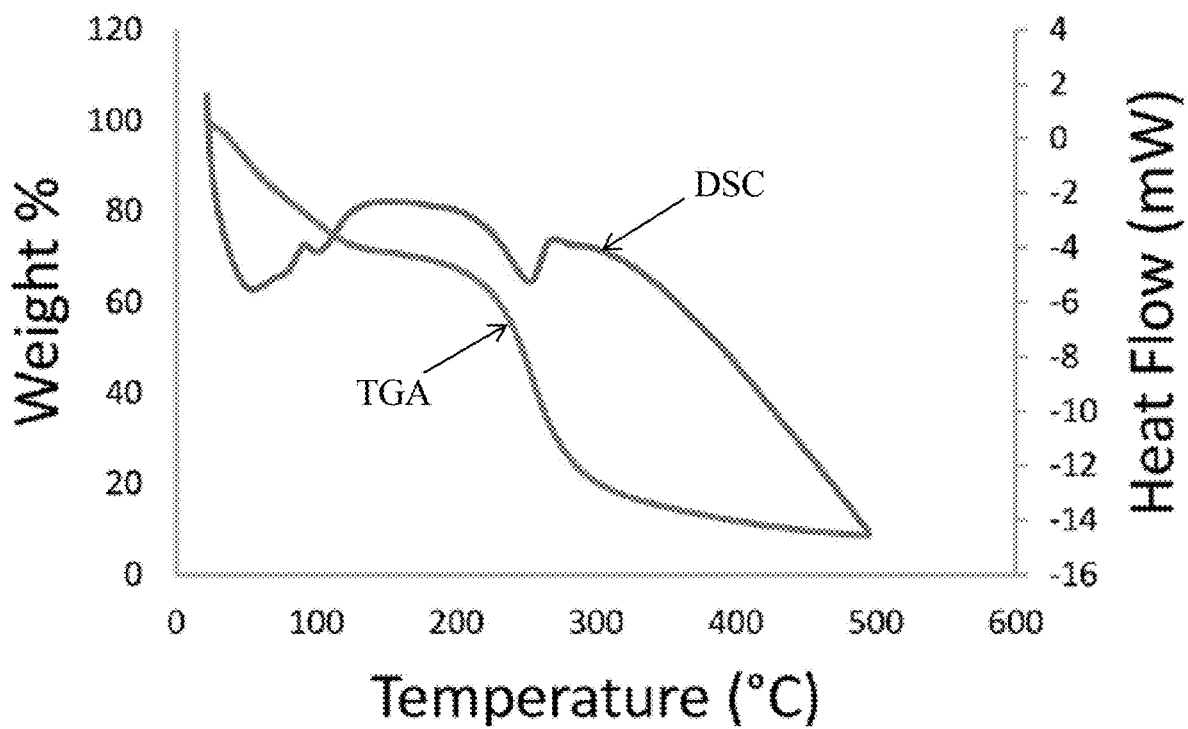
FIG. 5D is an overlay of TGA and DSC of the ionic liquid (III).

All three weight loss steps are accompanied by an endothermic change as can be seen from the DSC data (FIGS. 5A-D). Similarly, the thermal analysis (TGA, DTG and DSC) of compound 3 [or (III)] data has been obtained. Consequently, FIG. 5C shows overlap of thermogravimetric (TGA) graph and its first derivative (DTG) and FIG. 5D shows overlap of TGA and DSC graphs. As the compound is heated from ambient temperature to 140° C. a weight loss of 32% is observed, this is most likely due to the loss of water. After this step, the decomposition is observed in the temperature range from 200° C. to 340° C., during which the remaining weight loss (52%) is observed. The decomposition temperature calculated from DTG is 260° C. This step is accompanied by an endothermic change as can be seen from the DSC data (FIG. 5D).

Example 7

Procedure for Substituted Tetrahydro-1H-Carbazole (Indoles)/Methyl Tetrahydro-1H-Carbazole (Indolenines) Synthesis In a general procedure, an oven dried round bottomed flask was charged with corresponding phenyl hydrazine hydrochloride (1 mmol, 1 equiv.) and ethanol (3 mL). To the resulting solution corresponding 43uinolone43one/methyl cyclohxanone (1 mmol, 1 equiv.) and 4-(dimethylamino)-1-pentylpyridin-1-ium fluoride (2) [or (II)] (0.2 mmol, 0.2 equiv.) was added at room temperature and mixture was heated at reflux (78-80° C.) under nitrogen atmosphere. The consumption of starting material was monitored by thin layered chromatography by using eluents ethyl acetate/hexane (3:7). The crude reaction mixture was directly purified by silica gel column chromatography by using eluents in gradient eluents EtOAc/Hexane (1:9 to 1:1) to get the corresponding pure products (6a-h) in different yields.

Example 8

Spectral Data of Indolenines 6a-h (i) 2,3,4,9-Tetrahydro-1H-carbazole (6a)

Yield 89%. $^1$H NMR (400 MHz, DMSO-d$_6$): $\delta_H$ 10.58 (1H, s, NH), 7.30 (1H, d, J=7.6 Hz, ArH), 7.20 (1H, d, J=8 Hz, ArH), 6.96 (1H, t, J=7.2 Hz, ArH), 6.89 (1H, t, J=7.6 Hz, ArH), 2.68 (2H, t, J=5.6 Hz, CH$_2$), 2.60 (2H, t, J=5.4 Hz, CH$_2$), 1.82-1.79 (4H, m, (CH$_2$)$_2$) ppm; MS-EI m/z 171.1 (M$^+$). The data is identical to those previously reported [S. Gore, S. Baskaran, B. KOnig, Org. Lett., 14 (2012) 4568-4571, incorporated herein by reference in its entirety].

(ii) 6-Methoxy-2,3,4,9-tetrahydro-1H-carbazole (6b)
[S. Gore, S. Baskaran, B. Konig, Org. Lett., 14 (2012) 4568-4571, incorporated herein by reference in its entirety]

Yield 78%. $^1$H NMR (400 MHz, DMSO): $\delta_H$ 10.39 (1H, s, NH), 7.10 (1H, d, J=8.8 Hz, ArH), 6.81 (1H, d, J=2.0 Hz, ArH), 6.59 (1H, dd, J=8.4, 2.4 Hz, ArH), 3.71 (1H, s, OCH$_3$), 2.63 (2H, t, J=5.6 Hz, CH$_2$), 2.60 (2H, t, J=5.6 Hz, CH$_2$), 1.79-1.77 (4H, m, (CH$_2$)$_2$) ppm; MS-EI m/z 201 (M$^+$).

(iii) 6-Fluoro-2,3,4,9-tetrahydro-1H-carbazole (6c)
[P. P. Varma, B. S. Sherigara, K. M. Mahadevan, V. Hulikal, Synth. Commun., 39 (2008) 158-165; and S. Chandrasekhar, S. Mukherjee, Synth. Commun., 45 (2015) 1018-1022, Each Incorporated Herein by Reference in their Entirety]

Yield 74%. $^1$H NMR (300 MHz, DMSO-d$_6$): $\delta_H$ 10.69 (1H, s, NH), 7.19 (1H, dd, J=8.4, 3.8 Hz, ArH), 7.04 (1H, dd, J=10.0, 2.4 Hz, ArH), 6.76 (1H, td, J=9.6, 2.7 Hz, ArH), 2.67 (2H, t, J=5.4 Hz, CH$_2$), 2.56 (2H, t, J=5.4 Hz, CH$_2$), 1.82-1.75 (4H, m, CH$_2$—CH$_2$) ppm. MS-EI m/z 189.1 (M$^+$).

(iv) 6-Methoxy-1-methyl-2,3,4,9-tetrahydro-1H-carbazole (6d)

Yield 56%. $^1$H NMR (400 MHz, DMSO-d$_6$): $\delta_H$ 11.55 (1H, s, NH), 7.33 (1H, d, J=8.4 Hz, ArH), 6.99 (1H, d, J=2.4 Hz, ArH), 6.86 (1H, dd, J=8.4, 2.4 Hz, ArH), 3.76 (3H, s, OCH$_3$), 2.86-2.82 (1H, m, CH), 2.08 (1H, m, CHH), 1.81-1.78 (1H, m, CHH), 1.55 (1H, m, CH$_2$—CHH), 1.22 (3H, d, J=6.4 Hz, CH$_3$), 1.19-1.03 (3H, m, CH$_2$—CHH) ppm. MS-EI m/z 215.1 (M$^+$), EI-HRMS (M+) C$_{14}$H$_{17}$N$_1$O Found 215.1327, Calculated 215.1310.

(v) 8-Chloro-4a-methyl-2,3,4,4a-tetrahydro-1H-carbazole (6e)

Yield 76%. $^1$H NMR (400 MHz, DMSO-d$_6$): A 7.38 (1H, d, J=7.2 Hz, ArH), 7.34 (1H, d, J=8 Hz, ArH), 7.19 (1H, t, J=7.6 Hz, ArH), 2.71 (1H, app d, J=12.8 Hz, CHH), 2.66-2.58 (1H, m, CHH), 2.27 (1H, app d, J=13.2 Hz, CHH), 2.13 (1H, app d, J=13.2 Hz, CHH), 1.80-1.72 (1H, m, CHH—CH$_2$), 1.60 (1H, app d, J=13.6 Hz, CHH—CH$_2$), 1.34-1.26 (1H, m, CH$_2$—CHH), 1.27 (3H, s, CH$_3$), 1.01 (1H, td, J=13.2, 4 Hz, CH$_2$—CHH) ppm. MS-EI m/z 219.1 (M$^+$), 221.1, EI-HRMS (M$^+$) C$_{13}$H$_{14}$N$_1$Cl Found 219.0811, Calculated 219.0815.

(vi) 6-Cyano-2,3,4,9-tetrahydro-1H-carbazole (6f)

Yield 60%/o. $^1$H NMR (300 MHz, DMSO-d$_6$): $\delta_H$ 11.27 (1H, s, NH), 7.83 (1H, s, ArH), 7.38 (1H, d, J=8.4 Hz, ArH), 7.31 (1H, dd, J=8.4, 1.5 Hz, ArH), 2.69 (2H, app t, J=6.4 Hz, CH$_2$), 2.64 (2H, t, J=5.7 Hz, CH$_2$), 1.81-1.74 (4H, m, CH$_2$—CH$_2$) ppm. MS-EI m/z 196.1 (M*).

(vii) 7-Bromo-4a-methyl-2,3,4,4a-tetrahydro-1H-carbazole (6g)

Yield 55%. $^1$H NMR (400 MHz, DMSO-d$_6$): $\delta_H$ 7.65 (1H, s J=7.6 Hz, ArH), 7.39-7.34 (2H, m, ArH), 7.64 (1H, d, J=8 Hz, ArH), 2.68-2.57 (2H, m, CH$_2$), 2.28 (1H, app dd, J=12.8, 2.4 Hz, CHH), 2.12 (1H, app d, J=12.8 Hz, CHH), 1.79-1.71 (1H, m, CHH—CH$_2$), 1.60 (1H, app d, J=14 Hz, CHH—CH$_2$), 1.31-1.21 (CHH—CH$_2$), 1.24 (3H, s, CH$_3$), 0.97 (1H, td, J=13.6, 4 Hz, CH$_2$—CHH) ppm. MS-EI m/z 263.2 (M$^t$), 265.2, EI-HRMS (M$^+$) C$_{13}$HI$_4$NIBr Found 263.0300, Calculated 263.0310.

(viii) 6-Methoxy-2,2-dimethyl-2,3-dihydro-1H-carbazol-4(9H)-one (6h) [D.-Q. Xu, J. Wu, S.-P. Luo, J.-X. Zhang, J.-Y. Wu, X.-H. Du, Z.-Y. Xu, Green Chem., 11 (2009) 1239-1246, Incorporated Herein by Reference in its Entirety]

Yield 17%. $^1$H NMR (400 MHz, DMSO-d$_6$): $\delta_H$ 11.66 (1H, s, NH), 7.43 (1H, d, J=2.4 Hz, ArH), 7.25 (1H, d, J=8.8 Hz, ArH), 6.76 (1H, t, J=8.8 Hz, ArH), 3.75 (3H, s, OCH$_3$), 2.80 (2H, s, CH$_2$), 2.30 (2H, s, CH$_2$), 1.07 (6H, s, (CH$_3$)$_2$) ppm.

Example 9

A General Procedure for Phenyl 1H-Tetrazole Synthesis

To an oven dried micro reaction vessel corresponding benzonitrile (1 mmol, 1 equiv.), trimethylsilyl azide (3 mmol, 3 equiv.) and DMAP-IL (2) [or (II)] (0.3 equiv.) were added at room temperature and then capped with septum for reaction. The vessel with reaction mixture was heated at 110-115° C. for 24 h until the complete consumption of starting material, judged thin layer chromatography. On cooling the reaction mixture was diluted with EtOAc (20 mL) and shaken with 1-2 M HCl (20 mL) in separating funnel. Organic layer was separated and aqueous layer was further extracted with EtOAc (15 mL). The combined organic layers were dried with MgSO$_4$, filter and evaporated in vacuo to get the crude material. For purification silica gel column chromatography with eluents EtOAc/Hexane (1:1) to get the pure 1H-tetrazoles (8a-8f) as off-white to white solids in 48-78% yield.

Example 10

Spectral data of 1H-tetrazoles 8a-8g (i) 5-Phenyl-1H-tetrazole (8a)

Yield 48%. $^1$H NMR (400 MHz, DMSO-d$_6$): $\delta_H$ 8.04-8.02 (2H, m, ArH), 7.60-7.58 (3H, m, ArH) ppm; MS-EI m/z 146 (M+). The data is identical to those previously reported [D. Amantini, R. Beleggia, F. Fringuelli, F. Pizzo, L. Vaccaro, J. Org. Chem., 69 (2004) 2896-2898, incorporated herein by reference in its entirety].

(ii) 5-(4'-Methylphenyl)-1H-tetrazole (8b) [H. Naeimi, S. Mohamadabadi, Dalton Trans., 43 (2014) 12967-12973, Incorporated Herein by Reference in its Entirety]

Yield 78%. $^1$H NMR (400 MHz, DMSO-d$_6$): A 7.91 (2H, d, J=8.4 Hz, ArH), 7.39 (2H, d, J=8.0 Hz, ArH), 2.38 (3H, s, CH$_3$) ppm; MS-EI m/z 160 (M$^+$).

(iii) 5-(4'-Chlorophenyl)-1H-tetrazole (8c) [H. Naeimi, S. Mohamadabadi, Dalton Trans., 43 (2014) 12967-12973; and V. Rama, K. Kanagaraj, K. Pitchumani, J. Org. Chem., 76 (2011) 9090-9095, Each Incorporated Herein by Reference in their Entireties]

Yield 59%. $^1$H NMR (400 MHz, DMSO-d$_6$): $\delta_H$ 8.06 (2H, d, J=8.4 Hz, ArH), 7.68 (2H, d, J=8.4 Hz, ArH) ppm; MS-EI m/z 180 (M$^+$).

(iv) 5-(4'-Bromophenyl)-1H-tetrazole (8d) [H. Naeimi, S. Mohamadabadi, Dalton Trans., 43 (2014) 12967-12973, Incorporated Herein by Reference in its Entirety]

Yield 68%. $^1$H NMR (400 MHz, DMSO-d$_6$): $\delta_H$ 7.96 (2H, d, J=8.4 Hz, ArH), 7.79 (2H, d, J=8.4 Hz, ArH) ppm; MS-EI m/z 223 (M$^+$), 225.

(v) 5-(4'-Methoxyphenyl)-1H-tetrazole (8e) [O. Marvi, A. Alizadeh, S. Zarrabi, Bull. Korean Chem. Soc., 32 (2011) 4001, incorporated herein by reference in its entirety]

Yield 70%. $^1$H NMR (400 MHz, DMSO-d$_6$): $\delta_H$ 7.97 (2H, d, J=8.8 Hz, ArH), 7.14 (2H, d, J=8.8 Hz, ArH), 3.83 (3H, s, OCH$_3$) ppm; MS-EI m/z 176 (M+).

(vi) 5-(4'-Fluorophenyl)-1H-tetrazole (8f) [Z. Du, C. Si, Y. Li, Y. Wang, J. Lu, Int. J. Mol. Sci., 13 (2012) 4696-4703, incorporated herein by reference in its entirety]

Yield 58%. $^1$H NMR (400 MHz, DMSO-d$_6$): $\delta_H$ 8.07 (2H, dd, J=8.8, 5.6 Hz, ArH), 7.45 (2H, t, J=8.8 Hz, ArH) ppm; MS-EI m/z 164 (M$^+$).

Example 11

Theoretical Studies of DMAP-ILs 2 and 3 [or (II) and (III)]: Bulk Properties

Figure 6:
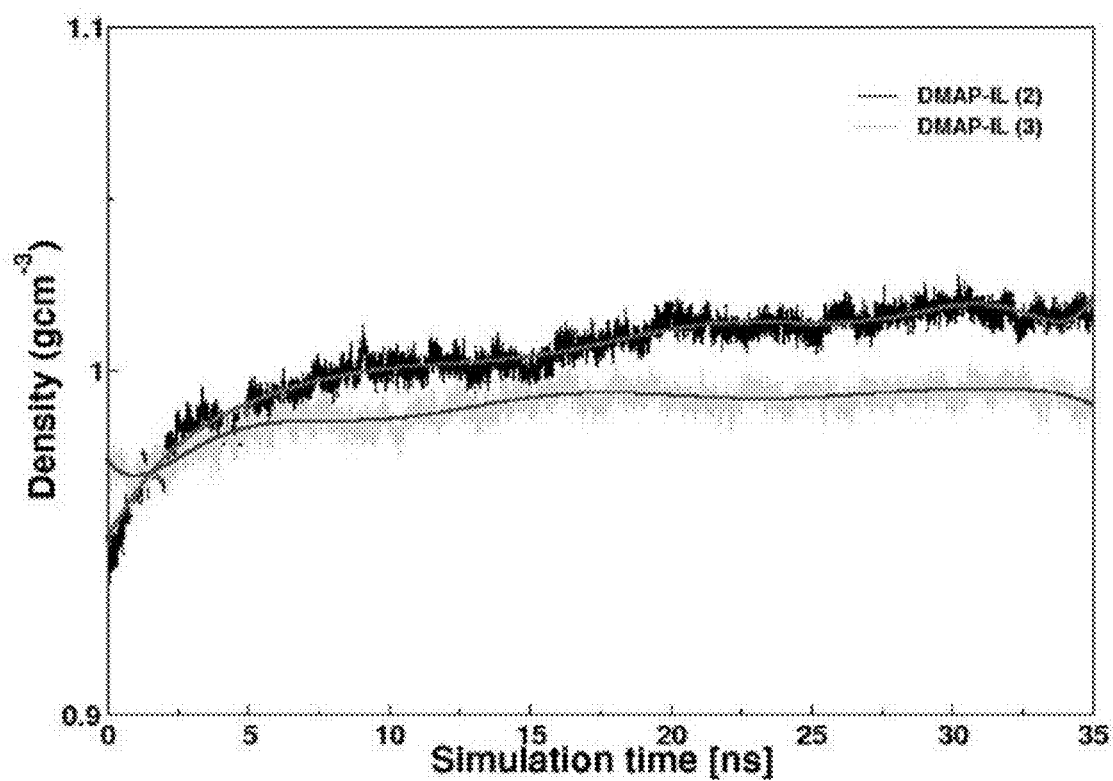
FIG. 6 illustrates densities of ionic liquids (II) [or: DMAP-IL (2)] and (III) [or: DMAP-IL (3)] as a function of time.

Molecular dynamics simulations were carried out to investigate the bulk properties of DMAP based ionic liquids, such as density, structural and transport properties which could further help in expanding the application of DMAP-based ionic liquids. Similarly, the newly synthesized DMAP based ionic liquids demonstrated their significances as catalysts, yet further applications of these ionic liquids would depend on the bulk properties which were evaluated via molecular dynamics simulations. FIG. 6 illustrates variation of densities of DMAP-ILs (2) and (3) [or (II) and (III)] at room temperature as a function of time. Average densities of 1.00±0.02 and 0.99±0.02 g cm-3 were obtained for DMAP-Ils (2) and (3) [or (II) and (III)] at room temperature, thus showing no effect of the alkyl chain lengthening in the two ionic liquids.

Figure 7:
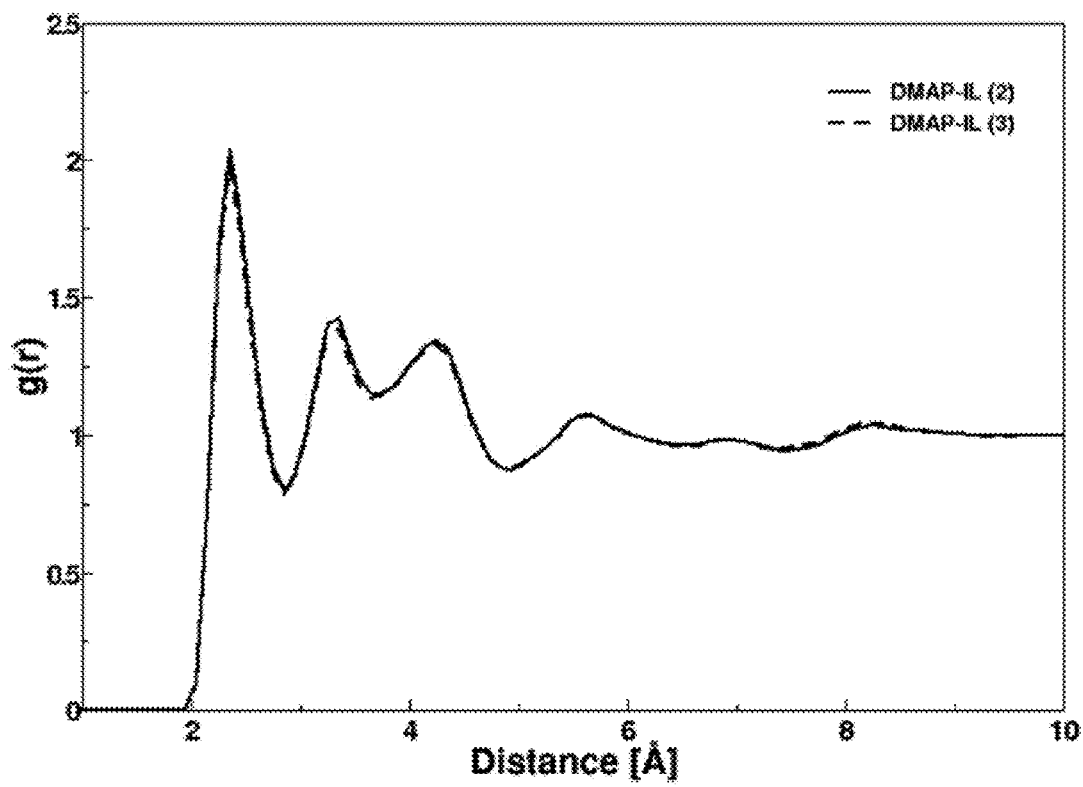
FIG. 7 depicts radical distribution functions between center of masses of cation and anion in ionic liquids (II) [or: DMAP-IL (2)] and (Ill) [or: DMAP-IL (3)].

The structural attributes of DMAP Ils (2) and (3) [or (II) and (III)] were primarily analyzed via radial distribution functions (RDFs) plotted between center of mass of cations and anions i.e. pyridinium and fluoride ions. FIG. 7 depicts the RDF profiles of cation-anion interaction in both cases, minimal distances of 2.35 Å were deduced from the first peak of both RDFs. The RDF patterns were very much similar to that of 48uinolone based ionic liquids previously investigated by us [N. Iqbal, J. Hashim, S. A. Ali, M. al-Rashida, R. D. Alharthy, S. Ahmad, K. M. Khan, F. Z. Basha, S. T. Moin, A. Hameed, RSC Adv., 5 (2015) 95061-95072, incorporated herein by reference in its entirety], thus demonstrating that the size and structural features of the cation had no significant influence on the cation-anion interaction. The first peaks were continued to well-structured second and third shell peaks at 3.32 and 4.26 Å along with few more peaks showing a long range influence of cations on anion or vice versa. A very sharp first peak was attributed to the strong electrostatic attraction between cations and their respective anions whereas second and third peak with low density corresponded to electrostatic interaction between cations and anions of opposite ion pairs.

Figure 8A:
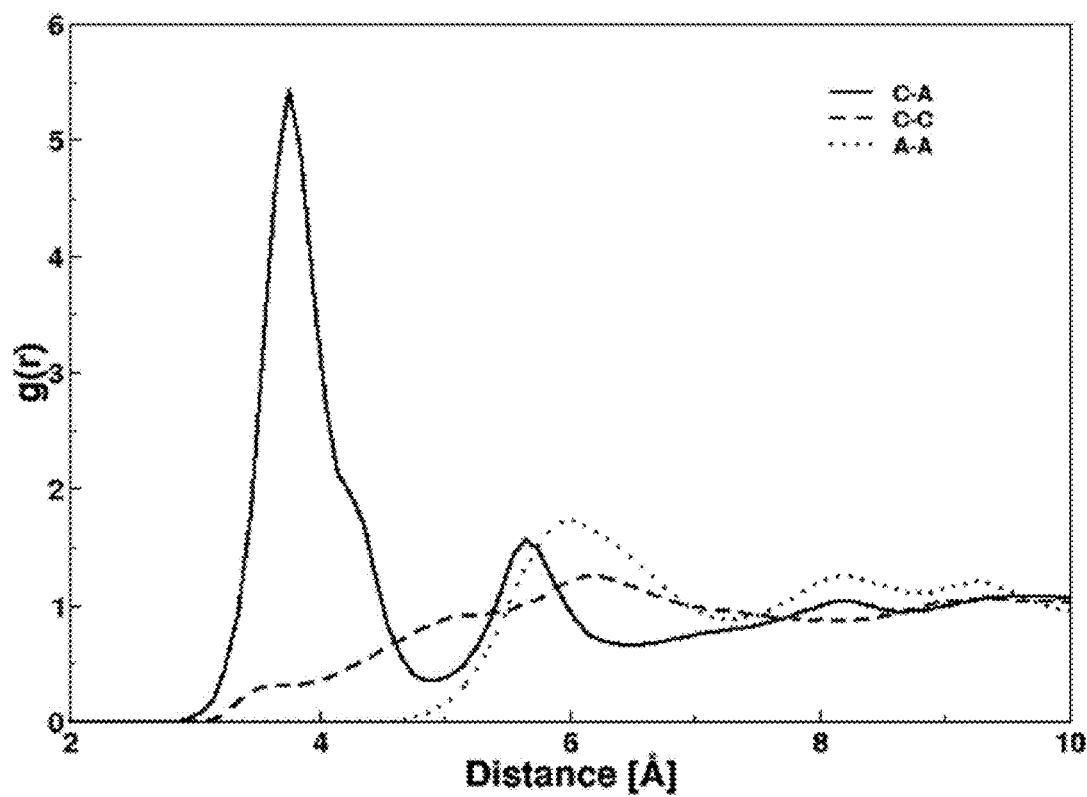
FIG. 8A illustrates radical distribution functions between N atoms of pyridinium ions (C—C), between fluoride ions (A-A), and between N atoms of pyridinium ions and fluoride ions (C-A) of the ionic liquid (II).
Figure 8B:
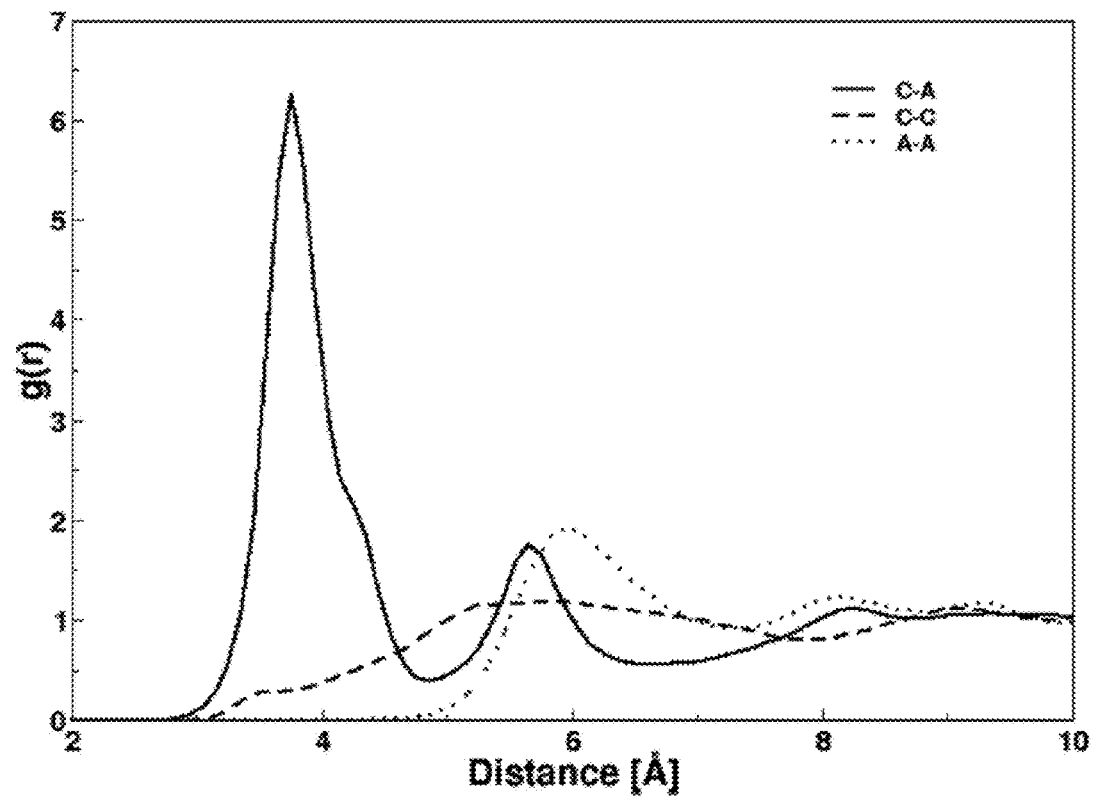
FIG. 8B illustrates radical distribution functions between N atoms of pyridinium ions (C—C), between fluoride ions (A-A), and between N atoms of pyridinium ions and fluoride ions (C-A) of the ionic liquid (III).

To further resolve the characteristic differences between the two DMAP ionic liquids i.e. compounds 2 and 3 [or (II) and (III)], RDFs were plotted between atomic pairs of cations and anions as shown in FIGS. 8A and 8B. The distribution function between nitrogen atoms of pyridinium ion and fluoride ions ($g_{C-A}$) in DMAP Ils (2) and (3) [or (II) and (III)] exhibited identical well-defined first peaks with maxima at 3.75 Å, which demonstrates the strong attraction between cations and anions based on electrostatics forces. A difference in the $g_{C-A}$ profile of the two ionic liquids was observed, and that difference was a bit higher intensity of the first peak in case of DMAP (3) [or (III)], as compared to its corresponding DMAP derivative. The $g_{C-A}$ profile yielded a tiny shoulder peak at ~4.35 Å along with the first peak which was attributed to the electron delocalization of the dimethyl amine attached to pyridinium ring that undergoes isomerization to produce dimethyl ammonium ion—a typical isomer of DMAP which may interact with fluoride ions and is involved in a number of catalytic reactions. Moreover, a similar trend was observed in the distribution functions of both ionic liquids between nitrogen atoms of pyridinium ions ($g_{C-C}$) and fluoride ($g_{A-A}$) ions—no peak was observed in the $g_{C-C}$ profile indicating no structure ordering of the pyridinium ions which may be due to strong repulsion between cations whereas first peak appeared at 5.96 Å in case of $g_{A-A}$ profile of fluoride ions.

Figure 9:
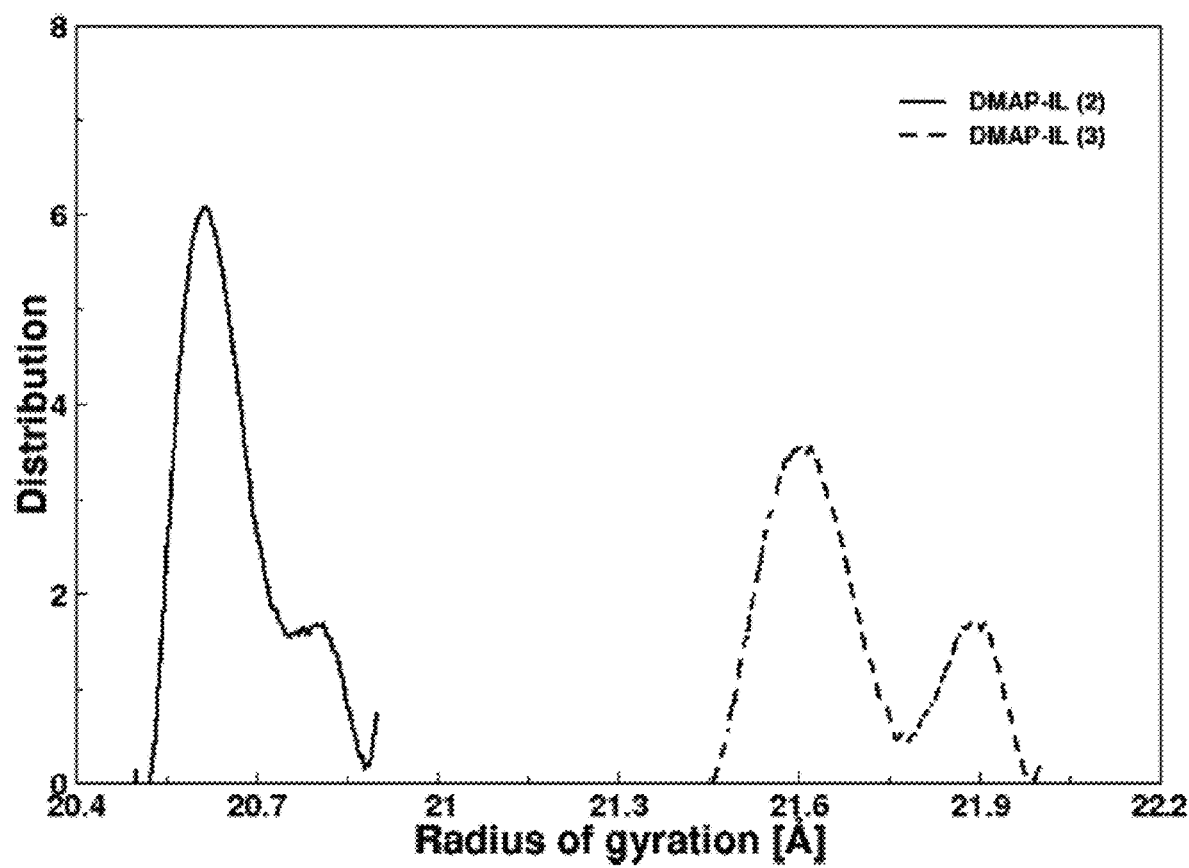
FIG. 9 depicts the distribution of radius of gyration of ionic liquids (II) [or: DMAP-IL (2)] and (III) [or: DMAP-IL (3)].

Both ionic liquids presented identical structural properties evaluated via radial distribution functions, nevertheless it was significant to assess the effect of alkyl chain length that was made possible by the evaluation of radius of gyration ($R_g$) of the two ionic liquids. FIG. 9 depicts the distribution of the radius of gyration obtained from MD simulation of DMAP Ils (2) and (3) [or (II) and (III)]. The $R_g$ distribution plot yielded the most probable values of 20.6 and 21.6 Å for DMAP (2) and (3) [or (II) and (III)], respectively. In both plots, shoulder peaks were visible at 20.8 and 21.9 Å showing the flexibility of alkyl side chain of different length. This further encouraged us to evaluate the transport properties of both ionic liquids, since transport properties were reported to be dependent on the alkyl side chain attached to core structure of different scaffolds.

Figure 10A:
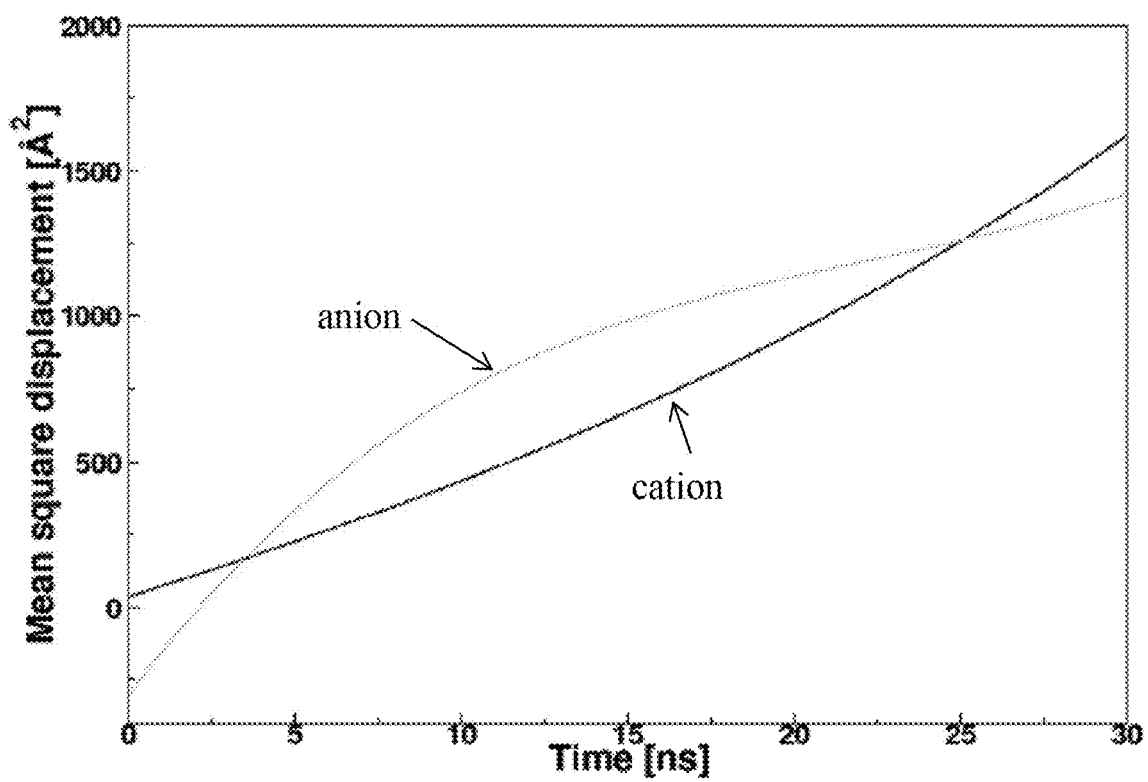
FIG. 10A illustrates mean-square displacement of the pyridinium and fluoride ions of the ionic liquid (II).
Figure 10B:
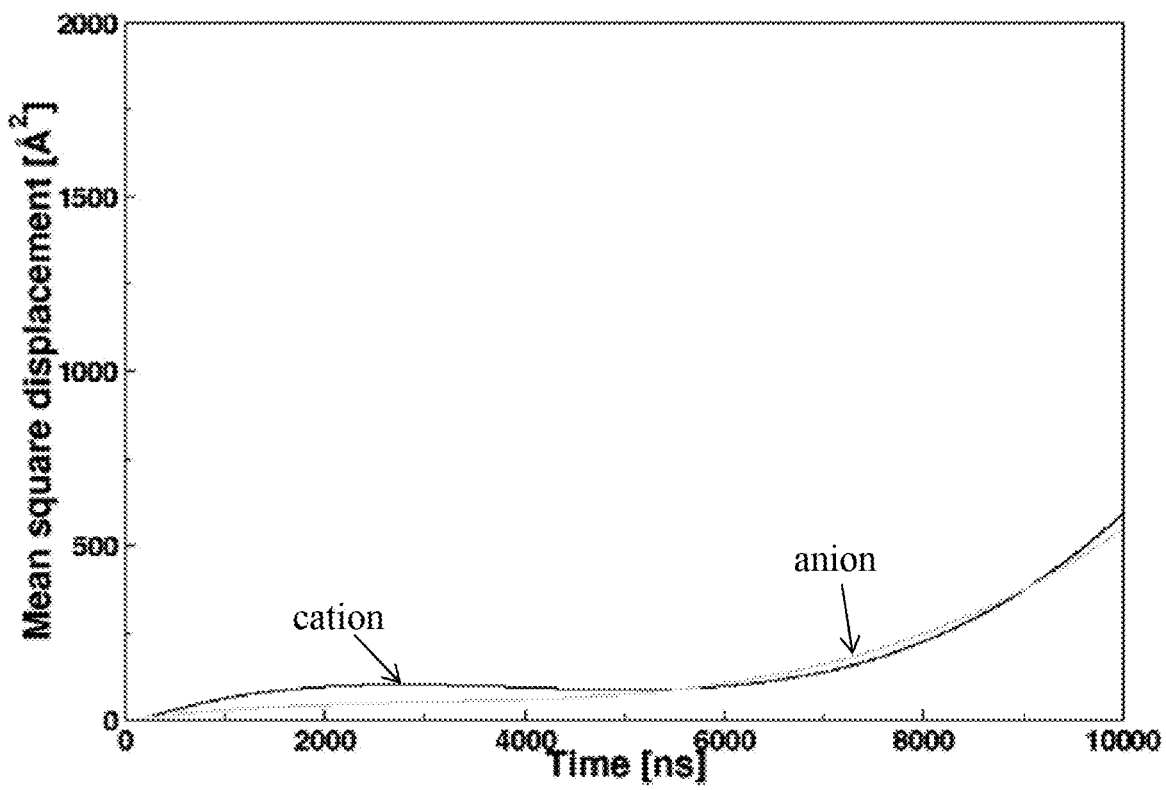
FIG. 10B illustrates mean-square displacement of the pyridinium and fluoride ions of the ionic liquid (III).
Figure 11A:
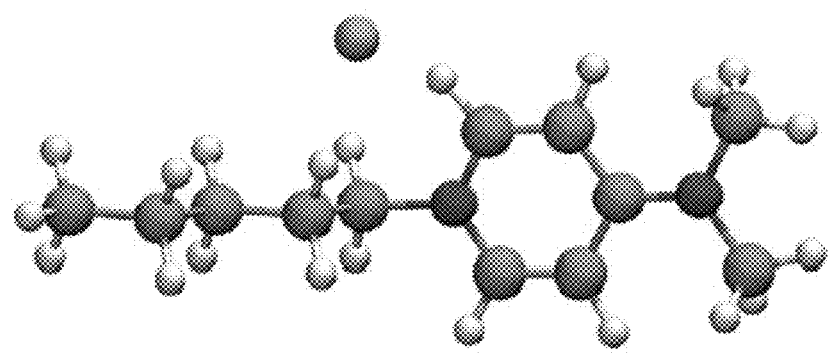
FIG. 11A is a structure of the ionic liquid (II) optimized at the Hartree-Fock (HF) level.
Figure 11B:
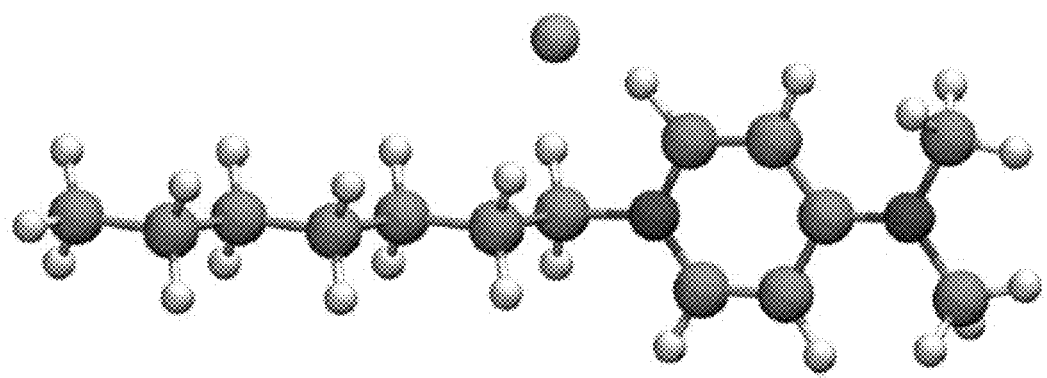
FIG. 11B is a structure of the ionic liquid (III) optimized at the HF level.

FIGS. 10A and 10B illustrate the mean square displacement (MSD) of the pyridinium and fluoride ions in the DMAP Ils (2) and (3) [or (II) and (III)], as obtained from MD simulations. The influence of alkyl chains of different length on the transport properties of DMAP based ionic liquids were demonstrated via MSD analysis that produced asymptotic plots similar to those observed in case of quinolinium based ionic liquids. The transport properties of cations with two different alkyl chains were reported to affect the properties of anions, therefore, a somewhat similar behavior was presumed for DMAP based ionic liquids. The MSD plots for the two ionic liquids presented a contrasting behavior, since the mean square displacement of both ions in the DMAP (2) was higher, indicating the fast motion of the alkyl side chain (cf. FIG. 8a). For the DMAP (3), the alkyl side chain did not follow the same trend, since low chain motion was deduced from the MSD plot shown in FIG. 8b. This could be due to strong electrostatic interactions between cations and anions thus resulting in ionic packing and restricting the fast motion of the alkyl chain. From the MSD plot, self-diffusion coefficients (D) were computed using the Einstein relation:

$$2nD = \lim_{t \to \infty}\left(\frac{MSD}{t}\right),$$

where n denotes the number of dimensions and it is equal to 3 in these cases whereas D represents diffusion coefficient.

Applying fitting procedure to the MSD plots with asymptotic linear region up to 2 ns corresponding to diffusion properties for pyridinium and fluoride ions, self-diffusion coefficients (D) were computed from the MSD slopes overs 0-2 ns. The coefficient values for pyridinium and fluoride ions in DMAP (2) [or (II)] were computed as $1.92 \pm 0.01 \times 10^{-6}$ and $6.09 \pm 0.14 \times 10^{-6}$ cm$^2$ s$^{-1}$, respectively. In the case of DMAP IL (3) [or (III)], comparatively lower values of self-diffusion coefficients were obtained ($0.92 \pm 0.06 \times 10^{-6}$ and $0.38 \pm 0.03 \times 10\text{-}6$ cm$^2$ s$^{-1}$ for pyridinium and fluoride ions, respectively). The coefficient value of the fluoride ion in DMAP IL (3) was lower in comparison to that of DMAP IL (2), correlating with the corresponding RDF data ($g_{C-A}$), attributing the strong electrostatic interaction between cations and anions, thus affecting the mobility of the fluoride ions.

Example 12

Theoretical Studies of DMAP-Ils 2 and 3 [or (II) and (III)]: Stability

Thermal stability of ionic liquids directs their applications in a number of industrial processes, therefore the evaluation of thermal stabilities of DMAP based ionic liquids was carried out in terms of binding energies. The energy data was obtained by the application of MP2 method on the HF optimized structures of DMAP ILs (2) and (3) [or (II) and (III)]. A very close value of binding energies was obtained as listed in Table 2. Binding energy data obtained from the ab initio calculations was in excellent agreement with the thermogravimetric analysis for DMAP ILs (2) and (3) [or (II) and (III)] which yielded respective optimal decomposition temperatures of 265° C. and 260° C. thus showing identical stability of these compounds. The correlation between structural properties and thermodynamics properties in terms of radial distribution functions and binding energies of DMAP based ionic liquids was observed, since both the structural and thermodynamics properties of the two ionic liquids were very close yet differences in the self-diffusion coefficients for cations and anions indicated the influence of side chain dynamics on the transport properties. The influence of the side chain on the diffusion coefficients were correlated to gyration radius which clearly shows the difference in the side chain dynamics affecting the diffusion of cations and anions. Self-diffusion coefficients were reported to be linearly varied with the alkyl chain lengths [H. Tokuda, K. Hayamizu, K. Ishii, M. A. B. H. Susan, M. Watanabe, J. Phys. Chem. B, 109 (2005) 6103-6110, incorporated herein by reference in its entirety] but anomalies could be expected.

TABLE 2

Binding energies of DMAP based ionic liquids obtained from MP2 calculations

| DMAP-ILs | 2 | 3 |
|---|---|---|
| Energy (kcal mol$^1$) | 131.3 | 131.2 |

Example 13

Theoretical Methods

Ionic liquids have a wide range of applications in different disciplines including energy and biological sciences and the evaluation of physical properties of ionic liquids such as viscosity, melting point, boiling point etc. must be known prior to their applications. To evaluate these properties for the related applications a rational approach based on systematic methods is needed to design efficient ionic liquids consisting of appropriate ionic pairs. Among such properties, the transport properties vary significantly when subtle changes are made in the structure of cation and anion pairs [E. J. Maginn, Acc. Chem. Res., 40 (2007) 1200-1207, incorporated herein by reference in its entirety]. Other properties such as viscosity and conductance depends on the diffusivity of ions i.e. viscosity becomes low and conductance gets higher, as the diffusion of ions is fast, therefore, the estimation of diffusion of ions would be helpful for the designing of new ionic liquids [N. Stolwijk, S. Obeidi, Electrochim. Acta, 54 (2009) 1645-1653, incorporated herein by reference in its entirety]. Both structural and transport properties were extensively studied via molecular dynamics (MD) simulations [M. Kowsari, S. Alavi, B. Najafi, K. Gholizadeh, E. Dehghanpisheh, F. Ranjbar, Phys. Chem. Chem. Phys., 13 (2011) 8826-8837; and A. T. Nasrabadi, L. D. Gelb, J. Phys. Chem. B, 121 (2017) 1908-1921, each incorporated herein by reference in their entirety]. The simulation methods were successfully applied to obtain reliable information related to both structure and transport properties of ionic liquids. Self-diffusion properties were recently reported for newly synthesized quinolone based ionic fluoride salts (QuFs) using molecular dynamics simulations [N. Iqbal, J. Hashim, S. A. Ali, M. al-Rashida, R. D. Alharthy, S. Ahmad, K. M. Khan, F. Z. Basha, S. T. Moin, A. Hameed, RSC Adv., 5 (2015) 95061-95072, incorporated herein by reference in its entirety]. A similar procedure was adopted to evaluate structure and transport properties of DMAP based ionic liquids in bulk. Self-diffusion coefficients and viscosities of these ionic liquids were also computed. The stability of ionic liquids is of prime importance. Therefore, binding energies were computed for the DMAP ionic liquids using the second order Møller-Plesset (MP2) perturbation theory method. A similar protocol was followed for the theoretical investigation of DMAP based ionic liquids that was successfully applied to quinolone based ionic fluoride salts (QuFs) [N. Iqbal, J. Hashim, S. A. Ali, M. al-Rashida, R. D. Alharthy, S. Ahmad, K. M. Khan, F. Z. Basha, S. T. Moin, A. Hameed, RSC Adv., 5 (2015) 95061-95072, incorporated herein by reference in its entirety].

(i) Binding Energy Calculations

Prior to binding energy calculations, both DMAP (2) and (3) [or (II) and (III)]derivatives were optimized at the Hartree-Fock level of theory using 6-31 G(d,p) basis sets for all atoms without the application of symmetry constraints. The binding energies of both derivatives were calculated at MP2 level of theory and 6-311G(d,p) basis sets were utilized for all atoms in order to evaluate thermal stabilities of these compounds. All ab initio calculations were performed using Gaussian 09 software [M. Frisch, G. Trucks, H. Schlegel, G. Scuseria, M. Robb, J. Cheeseman, G. Scalmani, V. Barone, B. Mennucci, G. Petersson, Gaussian 09, in, Gaussian, Inc., Wallingford Conn., 2009].

(ii) Molecular Dynamics Simulations

The initial configuration of the simulation boxes of DMAP (2) and (3) ionic liquids [or (II) and (III)] were prepared using the optimized structures of these derivatives as shown FIGS. 10A and 10B. Both DMAP derivatives were modeled with Generalized Amber Force Field (GAFF) [J. Wang, R. M. Wolf, J. W. Caldwell, P. A. Kollman, D. A. Case, J. Comput. Chem., 25 (2004) 1157-1174, incorporated herein by reference in its entirety] and Restrained Electrostatic Potential (RESP) charges [C. I. Bayly, P. Cieplak, W. Cornell, P. A. Kollman, J. Phys. Chem., 97 (1993) 10269-10280; and P. Cieplak, W. D. Cornell, C. Bayly, P. A. Kollman, J. Comput. Chem., 16 (1995) 1357-1377, each incorporated herein by reference in their entirety] were obtained. Simulation boxes consisting of 200 ion pairs of DMAP derivatives were constructed in defined regions of space using Packmol program [L. Martinez, R. Andrade, E. G. Birgin, J. M. Martinez, J. Comput. Chem., 30 (2009) 2157-2164, incorporated herein by reference in its entirety].

Prior to performing MD simulations, both systems were subjected to 10,000 steps of energy minimizations which were then followed by NVT equilibration for 15 ns. Afterwards, both systems were subjected to production MD for 40 ns including NPT equilibration and sampling of simulation trajectories. All bonds including hydrogen bonds were kept, thus enabling to use time step of 1.0 fs throughout the simulation. Long range electrostatic interactions were treated by applying Particle mesh Ewald algorithm and for non-bonded interactions, a cutoff value of 8.0 Å was used. The temperature was controlled at ~298 K using Langevin thermostat with collision frequency of 5.0 ps$^{-1}$, and pressure coupling algorithm with a relaxation time pf 1.0 ps was employed to maintain the pressure. Both MD simulation were performed using SANDER module of AMBERTOOLS17 whereas analysis of simulation trajectories were carried out by the CPPTRAJ module of AMBERTOOLS17 [D. A. Case, T. E. Cheatham, T. Darden, H. Gohlke, R. Luo, K. M. Merz, A. Onufriev, C. Simmerling, B. Wang, R. J. Woods, AMBER 17, in, University of California, San Francisco, 2017, incorporated herein by reference in its entirety]. For the visualization of simulation trajectories, VMD [W. Humphrey, A. Dalke, K. Schulten, J. Mol. Graph., 14 (1996) 33-38, incorporated herein by reference in its entirety] were used.

The invention claimed is:

1. An ionic liquid, which is at least one selected from the group consisting of

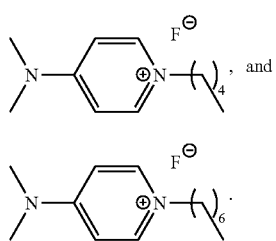

2. A method of synthesizing an ionic liquid of formula (I)

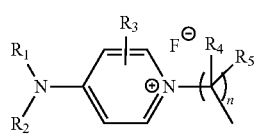

or a solvate thereof, a tautomer thereof, a stereoisomer thereof, or a mixture thereof, the method comprising:
reacting a pyridine compound of formula (IV)

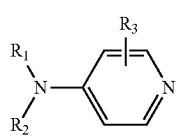

or a salt thereof, a solvate thereof, a stereoisomer thereof, or a mixture thereof with an alkyl halide of formula (V)

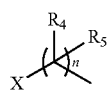

or a salt thereof, a solvate thereof, a stereoisomer thereof, or a mixture thereof to obtain a N-alkylated pyridinium halide; and
treating the N-alkylated pyridinium halide with a fluoride salt, thereby forming the ionic liquid of formula (I), wherein in formulae (I), (IV), and (V):
$R_1$ and $R_2$ are independently selected from the group consisting of an optionally substituted alkyl, an optionally substituted cycloalkyl, an optionally substituted arylalkyl, and an optionally substituted aryl;
$R_3$ is selected from the group consisting of a hydrogen, an optionally substituted alkyl, an optionally substituted cycloalkyl, an optionally substituted arylalkyl, an optionally substituted aryl, an optionally substituted alkoxy, an optionally substituted alkanoyl, an optionally substituted aroyl, a halogen, a nitro, and a cyano;
$R_4$ and $R_5$ are independently selected from the group consisting of a hydrogen, an optionally substituted alkyl, an optionally substituted cycloalkyl, an optionally substituted arylalkyl, and an optionally substituted aryl;
X is a chloride, a bromide, or an iodide; and
n is an integer in a range of 0-15.

3. The method of claim 2, wherein a molar ratio of the pyridine compound of formula (IV) to the alkyl halide of formula (V) is in a range of 1:2 to 2:1.

4. The method of claim 2, wherein the fluoride salt is at least one selected from the group consisting of transition metal fluorides, alkali metal fluorides, ammonium fluoride, and hydrogen fluoride.

5. The method of claim 2, wherein the fluoride salt is silver fluoride.

6. A method of synthesizing an indole or indolenine, the method comprising reacting an aryl hydrazine with an alkyl ketone or an alkyl aldehyde in the presence of the ionic liquid of claim 1, thereby forming the indole or indolenine.

7. The method of claim 6, wherein a molar ratio of the aryl hydrazine to the alkyl ketone or the alkyl aldehyde is in a range of 1:2 to 2:1, and wherein the ionic liquid is present in an amount of 5 mol % to 40 mol % relative to moles of the aryl hydrazine.

8. The method of claim 6, wherein the reacting is conducted at a temperature in the range of 60° C. to 120° C.

9. The method of claim 6, wherein the indole and indolenine is at least one selected from the group consisting of

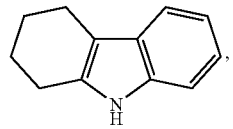

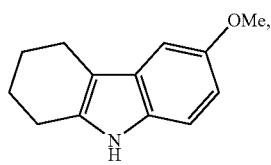

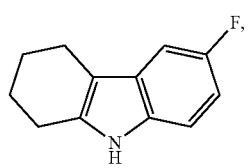

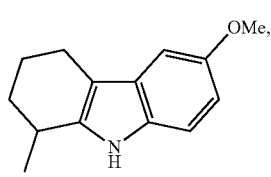

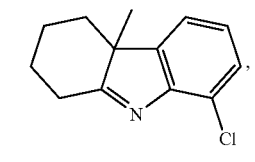

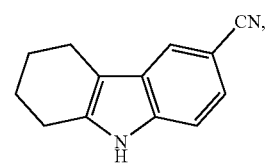

-continued

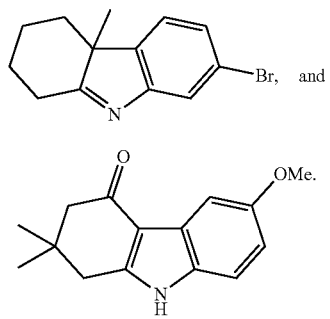
(6g)

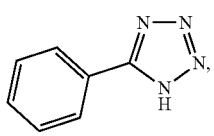
(6h)

10. A method of synthesizing a tetrazole, the method comprising reacting a nitrile with an azide in the presence of the ionic liquid of claim 1, thereby forming the tetrazole.

11. The method of claim 10, wherein a molar ratio of the nitrile to the azide is in a range of 1:2 to 1:6, and wherein the ionic liquid is present in an amount of 10 mol % to 50 mol % relative to moles of the nitrile.

12. The method of claim 10, wherein the reacting is conducted at a temperature in the range of 80° C. to 150° C.

13. The method of claim 10, wherein the tetrazole is at least one selected from the group consisting of (8a)

-continued (8b)

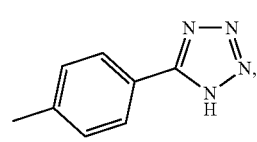

(8c)

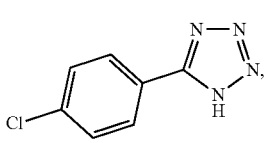

(8d)

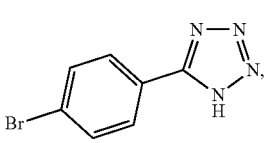

(8e)

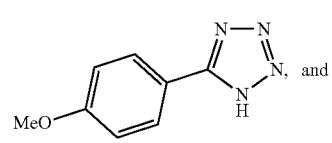

(8f)

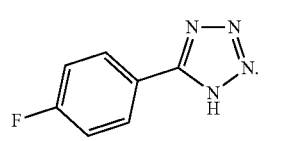

* * * * *

UNITED STATES PATENT AND TRADEMARK OFFICE
CERTIFICATE OF CORRECTION

PATENT NO. : 10,577,327 B2
APPLICATION NO. : 16/004511
DATED : March 3, 2020
INVENTOR(S) : Sarfaraz Ali Ghumro et al.

It is certified that error appears in the above-identified patent and that said Letters Patent is hereby corrected as shown below:

On the Title Page

Item (72), the Inventors' information is incorrect. Item (72) should read:
--(72) Inventors: Sarfaraz Ali Ghumro, Karachi (PK); Rima D. Alharthy, Jeddah (SA); Sana Saleem, Karachi (PK); Mariya Al-Rashida, Lahore (PK); Nafees Iqbal, Karachi (PK); Shakil Ahmed, Karachi (PK); Syed Abid Ali, Karachi (PK); Syed Tarique Moin, Karachi (PK); Abdul Hameed, Lahore (PK)--

Signed and Sealed this
Second Day of June, 2020

Andrei Iancu
*Director of the United States Patent and Trademark Office*